United States Patent
De Ridder

(10) Patent No.: US 9,555,248 B2
(45) Date of Patent: Jan. 31, 2017

(54) SYSTEM AND METHOD FOR TACTILE C-FIBER STIMULATION

(71) Applicant: Dirk De Ridder, Dunedin (NZ)

(72) Inventor: Dirk De Ridder, Dunedin (NZ)

(73) Assignee: Advanced Neuromodulation Systems, Inc., Plano, TX (US)

(*) Notice: Subject to any disclaimer, the term of this patent is extended or adjusted under 35 U.S.C. 154(b) by 0 days.

(21) Appl. No.: 14/850,066

(22) Filed: Sep. 10, 2015

(65) Prior Publication Data

US 2016/0074664 A1 Mar. 17, 2016

Related U.S. Application Data

(60) Provisional application No. 62/049,076, filed on Sep. 11, 2014.

(51) Int. Cl.
| | | |
|---|---|---|
| *A61N 1/00* | (2006.01) | |
| *A61N 1/36* | (2006.01) | |
| *A61N 1/05* | (2006.01) | |
| *A61N 1/372* | (2006.01) | |
| *A61N 1/378* | (2006.01) | |

(52) U.S. Cl.
CPC ......... *A61N 1/36185* (2013.01); *A61N 1/0551* (2013.01); *A61N 1/3787* (2013.01); *A61N 1/37264* (2013.01)

(58) Field of Classification Search
CPC .............. A61N 1/0551; A61N 1/36185; A61N 1/37264; A61N 1/3787
See application file for complete search history.

(56) References Cited

U.S. PATENT DOCUMENTS

| | | | |
|---|---|---|---|
| 7,337,005 B2 * | 2/2008 | Kim | A61N 1/0558 607/117 |
| 8,364,271 B2 | 1/2013 | De Ridder | |
| 8,364,273 B2 | 1/2013 | De Ridder | |
| 8,401,655 B2 | 3/2013 | De Ridder | |
| 8,682,441 B2 | 3/2014 | De Ridder | |
| 8,897,870 B2 | 11/2014 | De Ridder | |
| 8,934,981 B2 | 1/2015 | De Ridder | |
| 2015/0223721 A1 | 8/2015 | De Ridder | |

OTHER PUBLICATIONS

Jaquette Liljencrantz and Hakan Olausson; Tactile C fibers and their contributions to pleasant sensations and to tactile allodynia; Frontiers in Behavioral Neuroscience; Mar. 6, 2014; vol. 8; Article 37; 6 pages.

* cited by examiner

*Primary Examiner* — George Manuel

(57) ABSTRACT

A method is provided to deliver C tactile fiber stimulation to nervous tissue of a patient. The method comprises delivering a first tactile stimulation waveform to a first electrode combination within an array of electrodes located proximate to nervous tissue of interest. The method further provides sequentially delivering successive tactile stimulation waveforms to successive electrode combinations within the array of electrodes. The first and successive tactile stimulation waveforms include at least one series of pulses having a pulse amplitude and pulse frequency. Delaying delivery of the successive tactile stimulation waveforms by a firing delay, the pulse amplitude, pulse frequency and firing delay represent therapy parameters. The method manages at least one of the therapy parameters of the first and successive tactile stimulation waveforms to excite C tactile fibers of the nervous tissue of interest.

12 Claims, 8 Drawing Sheets

SYSTEM AND METHOD FOR TACTILE C-FIBER STIMULATION

CROSS-REFERENCE TO RELATED APPLICATIONS

The present application claims the benefit of U.S. Provisional Patent Application No. 62/049,076, filed on Sep. 11, 2014 and entitled "C-FIBER STIMULATION," the complete subject matter of which is incorporated herein by reference in its entirety.

BACKGROUND OF THE INVENTION

Embodiments of the present disclosure generally relate to neurostimulation (NS), and more particularly to delivering C tactile fiber stimulation.

NS systems are devices that generate electrical pulses and deliver the pulses to nervous tissue to treat a variety of disorders. For example, spinal cord stimulation has been used to treat chronic and intractable pain. Another example is deep brain stimulation, which has been used to treat movement disorders such as Parkinson's disease and affective disorders such as depression. While a precise understanding of the interaction between the applied electrical energy and the nervous tissue is not fully appreciated, it is known that application of electrical pulses to certain regions or areas of nervous tissue can effectively reduce the number of pain signals that reach the brain. For example, applying electrical energy to the spinal cord associated with regions of the body afflicted with chronic pain can induce "paresthesia" (a subjective sensation of numbness or tingling) in the afflicted bodily regions.

SCS therapy, delivered via epidurally implanted electrodes, is a widely used treatment for chronic intractable neuropathic pain of different origins. Traditional tonic therapy evokes paresthesia covering painful areas of a patient. During SCS therapy calibration, the paresthesia is identified and localized to the painful areas by the patient in connection with determining correct electrode placement.

Recently, new stimulation configurations such as burst stimulation and high frequency stimulation, have been developed, in which closely spaced high frequency pulses are delivered to the spinal cord in a manner that does not generate paresthesias for the majority of patients, but still affords a therapeutic result. Neuropathic pain may result from lesions or diseases affecting the peripheral or central regions of the somatosensory system, and is difficult to treat. The first spinal cord stimulator as a treatment for neuropathic pain was implanted by Shealy in 1967, which was based on the gate-control theory proposed by Melzack and Wall (1965). The gate-control theory proposed that the activation of large diameter A-beta (Aβ) fibers inhibits the transmission of noxious stimuli to the brain via an inhibitory interneuron. It has been shown that electrical stimulation also may activate these large A-beta fibers with the same result. The A-beta fibers transmit information from the periphery through the dorsal root ganglion (DRG) before projecting through the dorsal column.

Other types of sensory neurons (nerve cells) transmit information from the periphery. A-delta (A-delta) fibers are small lightly myelinated fibers that transmit mechanical or painful information, and may be perceived as the sharp pain felt after injury. C-fibers are smaller and unmyelinated sensory neurons that transmit painful information to spinothalamic tract neurons (major pain pathway) and may be perceived as the dull ache after injury.

In general, conventional neurostimulation systems seek to manage pain and other pathologic or physiologic disorders through stimulation of select nerve fibers that carry pain related signals. Conventional methods of neurostimulation essentially attempt to block pain related signals by applying a continuously train of pulses to respective nerve fibers.

SUMMARY

In accordance with embodiments herein a method is provided to deliver C tactile fiber stimulation to nervous tissue of a patient. The method comprises delivering a first tactile stimulation waveform to a first electrode combination within an array of electrodes located proximate to nervous tissue of interest. The method further provides sequentially delivering successive tactile stimulation waveforms to successive electrode combinations within the array of electrodes. The first and successive tactile stimulation waveforms include at least one series of pulses having a pulse amplitude and pulse frequency. The method delays delivery of the successive tactile stimulation waveforms by a firing delay. The pulse amplitude, pulse frequency and firing delay represent therapy parameters. The method manages at least one of the therapy parameters of the first and successive tactile stimulation waveforms to excite C tactile fibers of the nervous tissue of interest.

The firing delay represents a substantially quiescent period between the first and successive tactile stimulation waveforms. The series of pulses includes a group of spikes that begin and end at the pulse amplitude. The pulse amplitude is set to avoid excitation of nociceptive C fibers. The pulse amplitude corresponds to a lower threshold of an excitation range for nociceptive C fibers such that the first and successive tactile stimulation waveforms do not excite the nociceptive C fibers. The pulse amplitude is in the range of 0.3 to 2.5 mN, corresponding to the excitation range of C tactile fibers.

Optionally, the firing delay between successive pairs of the multiple tactile stimulation waveforms is between one and 10 cm/s. The delivering operations are repeated for multiple tactile stimulation waveforms in connection with corresponding electrode combinations in the array. Excitation of successive pairs of the multiple tactile stimulation waveforms is separated by the firing delay to correspond to a velocity at which C tactile fibers convey signals. The series of pulses are organized into pulse bursts. The electrode array represents a linear array of electrode combinations arranged along a length of an electrode body. The pulse frequency is approximately 40 Hz.

In accordance with embodiments herein a system is provided to control C tactile fiber stimulation of nervous tissue of a patient. The system comprises a lead having an array of stimulation electrodes. The lead is configured to be implanted at a target position proximate to nervous tissue of interest. The system further comprises an implantable medical device (IMD) coupled to the lead. The IMD includes a processor and memory storing programmable instructions. The processor executes the programmable instructions to sequentially deliver tactile stimulation waveforms to a series of electrode combinations within the array. The tactile stimulation waveforms include at least one series of pulses having a pulse amplitude and pulse frequency. The processor further executes the programmable instructions to delay delivery of the successive tactile stimulation waveforms relative to one another by a firing delay. The pulse amplitude, pulse frequency and firing delay represent therapy parameters. Further, the processor manages at least one of the therapy parameters such that the successive tactile stimulation waveforms excites C tactile fibers of the nervous tissue of interest.

The electrode combinations in the series are arranged along a body of the lead and positioned adjacent to one another. The processor delivers the tactile stimulation waveforms to the electrode combinations in a temporal serial manner such that adjacent electrode combinations deliver corresponding tactile stimulation waveforms at nonoverlapping distinct points in time. The processor sequentially steps through adjacent electrode combinations such that the tactile stimulation waveforms are progressively delivered at distinct activation sites along the lead at an activation rate corresponding to a corresponding non-noxious tactile input.

Optionally, the firing delay corresponds to an activation rate of between 1 and 10 cm/s. The firing delay is based on a spacing between the electrode combinations that are adjacent to one another. The IMD includes a pulse generator and a switch circuit that couples the pulse generator to a corresponding one of the electrode combinations when delivering a corresponding tactile stimulation waveform. The IMD includes a switch circuit that defines individual channels between the IMD and each of the electrode combinations. The tactile stimulation waveforms are delivered over corresponding channels at nonoverlapping points in time.

DETAILED DESCRIPTION

Figure 1A:
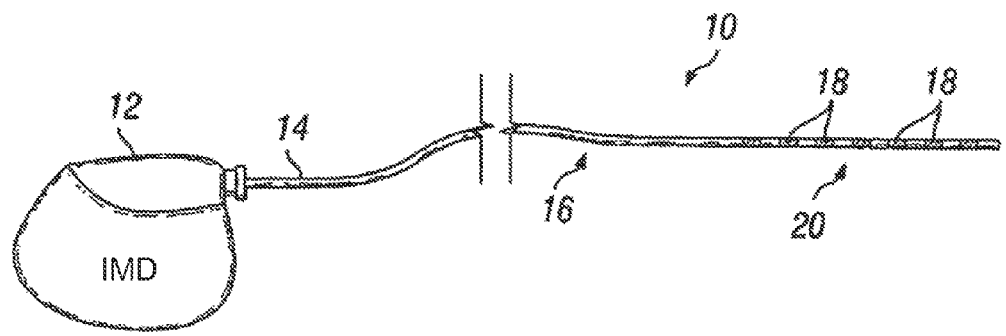
FIG. 1A illustrates an example neurological stimulation (NS) system for electrically stimulating a predetermined site area to treat one or more neurological disorders or conditions in accordance with embodiments herein.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

I. Definitions

Unless defined otherwise, technical and scientific terms used herein have the same meaning as commonly understood by one of ordinary skill in the art to which this invention belongs. For purposes of the description, the following terms are defined below. Further, additional terms are used herein that shall have definitions consistent with the definitions set forth in U.S. Pat. No. 8,401,655, which is expressly incorporated herein by reference in its entirety.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, the term "burst firing" or "burst mode" refers to an action potential that is a burst of high frequency spikes/pulses (e.g. 400-1000 Hz) (Beurrier et al., 1999). Burst firing acts in a non-linear fashion with a summation effect of each spike/pulse. One skilled in the art is also aware that burst firing can also be referred to as phasic firing, rhythmic firing (Lee 2001), pulse train firing, oscillatory firing and spike train firing, all of these terms used herein are interchangeable.

As used herein, the term "tonic firing" or "tonic mode" refers to an action potential that occurs in a linear fashion.

As used herein, the term "burst" refers to a period in a spike train that has a much higher discharge rate than surrounding periods in the spike train (N. Urbain et al., 2002). Thus, burst can refer to a plurality of groups of spike pulses. A burst is a train of action potentials that, possibly, occurs during a 'plateau' or 'active phase', followed by a period of relative quiescence called the 'silent phase' (Nunemaker, Cellscience Reviews Vol 2 No. 1, 2005.) Thus, a burst comprises spikes having an inter-spike interval in which the spikes are separated by 0.5 milliseconds to about 100 milliseconds. Those of skill in the art realize that the inter-spike interval can be longer or shorter. Yet further, those of skill in the art also realize that the spike rate within the burst does not necessarily occur at a fixed rate; this rate can be variable.

The terms "pulse" and "spike" are used interchangeably to refer to an action potential. Yet further, a "burst spike" refers to a spike that is preceded or followed by another spike within a short time interval (Matveev, 2000), in otherwords, there is an inter-spike interval, in which this interval is generally about 100 ms but can be shorter or longer, for example 0.5 milliseconds.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T11 nerve root leaves the spinal cord myelum at an area located behind vertebral body T8-T9 but leaves the bony spine between T11 and T12.

II. Nervous System

The nervous system comprises two general components, the central nervous system, which is composed of the brain and the spinal cord, and the peripheral nervous system, which is composed of ganglia or dorsal root ganglia and the peripheral nerves that lie outside the brain and the spinal cord. One of skill in the art realizes that the nervous system may be linguistically separated and categorized, but functionally they are interconnected and interactive.

The central nervous system comprises the brain and spinal cord, which together function as the principal integrator of sensory input and motor output. In general terms, the brain consists of the cerebrum (cerebral hemispheres and the diencephalons), the brainstem (midbrain, pons, and medulla); and the cerebellum. It is well known that the cerebrum represents the highest center for sensory and motor and emotional and cognitive processing. In general, the frontal lobe processes motor, visual, speech, and personality modalities; the parietal lobe processes sensory information; the temporal lobe, auditory and memory modalities; and the occipital lobe vision. The cerebellum, in general, coordinates smooth motor activities and processes muscle position, while the brainstem conveys motor and sensory information and mediates important autonomic functions. These structures are of course integrated with the spinal cord which receives sensory input from the body and conveys somatic and autonomic motor information to peripheral targets. Thus, one of skill in the art realizes that the central nervous system is capable of evaluating incoming information and formulating response to changes that threaten the homeostasis of the individual.

Types of Nerve Fibers

In general, the peripheral nerve fibers may be classified into three types of nerve fibers based on the nerve fiber diameter and conduction velocity, namely A-, B- and C-fibers. A-fibers have large diameters, high conduction velocities, are highly myelinated, and are further subdivided by size and conduction velocity as A-alpha, A-beta, A-gamma and A-delta fibers. By way of example, the fast conduction velocity of the A-alpha fibers may be on the order of 80-120 m/s, and the A-alpha fibers may be on average 13-20 µm in diameter. B-fibers have diameters of about 4 um and conduction velocities of 4-15 m/s. C-fibers are small neurons with slow conduction velocities and are not myelinated.

The A-beta fibers carry touch related information having high temporal and spatial resolution. The A-beta fibers "code" (e.g., are responsive to) all or most aspects of mechanstimulation. The A-beta fibers project through the posterior spinal column to the somatosensory cortices. The C fibers carry touch information with lower (relative to A-beta fibers) temporal and spatial resolution. The C fibers "code" (e.g., are responsive to) specific forces and velocities and project through the spinothalamic tract to the insular cortex.

A-delta fibers have conduction velocities on the order of 12 m/s, and the A-delta fibers may be on average 1.0-5.0 µm in diameter. A-delta fibers carry information mainly from the nociceptive-mechanical or mechanothermal-specific stimuli and are considered nociceptors. Their receptive fields (area of innervation) are small, and therefore, provide precise localization of pain (e.g., topgraphic, sharp, pricking, electric, acute).

C-fibers are unmyelinated, have a small diameter and low conduction velocity. By way of example, the slow conduction velocity of the C-fibers may be on the order of less than 1 m/s, and the C-fibers may be on average 0.2-1.5 µm in diameter. C-fibers carry non-topographic sensory information, such as nociception (pain), temperature, and itch. C-fibers carry "slow pain" sensory information such as dull pain, burning sensation, aching, throbbing and other chronic pains. C-fibers are unmyelinated unlike most other fibers in the nervous system. C-fibers are activated by and carry information from a variety of high-intensity mechanical, chemical and thermal stimulation and thus are considered as polymodal nociceptors. Nociception is the response to painful stimuli transmitted via sensory action potentials of A-delta and C-fibers.

There are two types of C fibers, namely nociceptive C fibers and low threshold mechanoreceptive C tactile fibers. The C nociceptive and tactile fibers are responsive to different sensations. The C tactile fibers contribute to pleasant touch and provide a sensory underpinning of social behavior. The C tactile fibers respond to indentation forces in the range of 0.3-2.5 mN. The C tactile fibers respond with high frequency to stimuli that are clearly innocuous, such as slow stroking with the experimenter's finger tips or a soft brush. In contrast, C nociceptor fibers have a mechanical threshold of greater that 2.5 mN.

The conduction velocity of C tactile fibers varies between 0.6-1.3 m/s. To a sustained indentation, C tactile fibers initially respond with a high frequency burst of impulses, however the firing rate decreases 20 within a few seconds (e.g. five seconds). Given the decreased firing rate, C tactile fibers are considered to have an intermediate adaptation characteristic as compared with the slower and rapidly adapting myelinated mechanoreceptors (slowly adapting units continue to fire during indentation whereas rapidly adapting units only fire when the skin deformation is changed). In a subset of the C tactile fibers, the response may increase again after the initial period of adaptation with firing continuing for 1 to 2 minutes until finally stopping (a phenomenon referred to as a delayed acceleration). In addition, C tactile fibers are considered relatively highly fatigable, in that when several identical stimuli are delivered to the same skin area, the response to the first stimulus is usually much larger than the responses to subsequent similar stimuli.

As one example, a caressing type of slowly moving touch is a particularly effective stimuli for C tactile fibers. Past research has shown that a maximum unit response may occur for movement velocities in the range of one-10 cm/s, whereas the unit response is weaker for slower or faster movements (Loken et al., 2009). In psychophysical experiments brushstrokes in the velocity range of one-10 cm/s were perceived as more pleasant than strokes with slower or faster velocities (Loken et al., 2009). Hence, a positive correlation exists between firing frequency of C tactile fibers and perceived pleasantness of soft brushstrokes (Loken et al., 2009).

Sensations may be characterized based on an amount of force applied against a patient's skin, a nature of the applied force, a location at which the force is applied to the patient's skin, and the like. The nature of the applied force may be characterized based on the type of instrument applying the force, a rate at which the force is applied and the directional nature of the force (e.g. a circular motion, a stroking motion, pressing upon a single point), among other things. For example, the nociceptive C fibers are responsive to higher threshold sensations (e.g., forces applied greater than 2.5 mN) such as pinches or a stabbing force, while the C tactile fibers are responsive to lower threshold sensations (e.g., forces applied in the range of 0.3-2.5 mN). The C tactile fibers are also responsive to forces having a directional nature, such as applying contact with a force in the appropriate range while moving the contact along a path (e.g. gentle caressing, nurturing, grooming touch).

Figure 6:
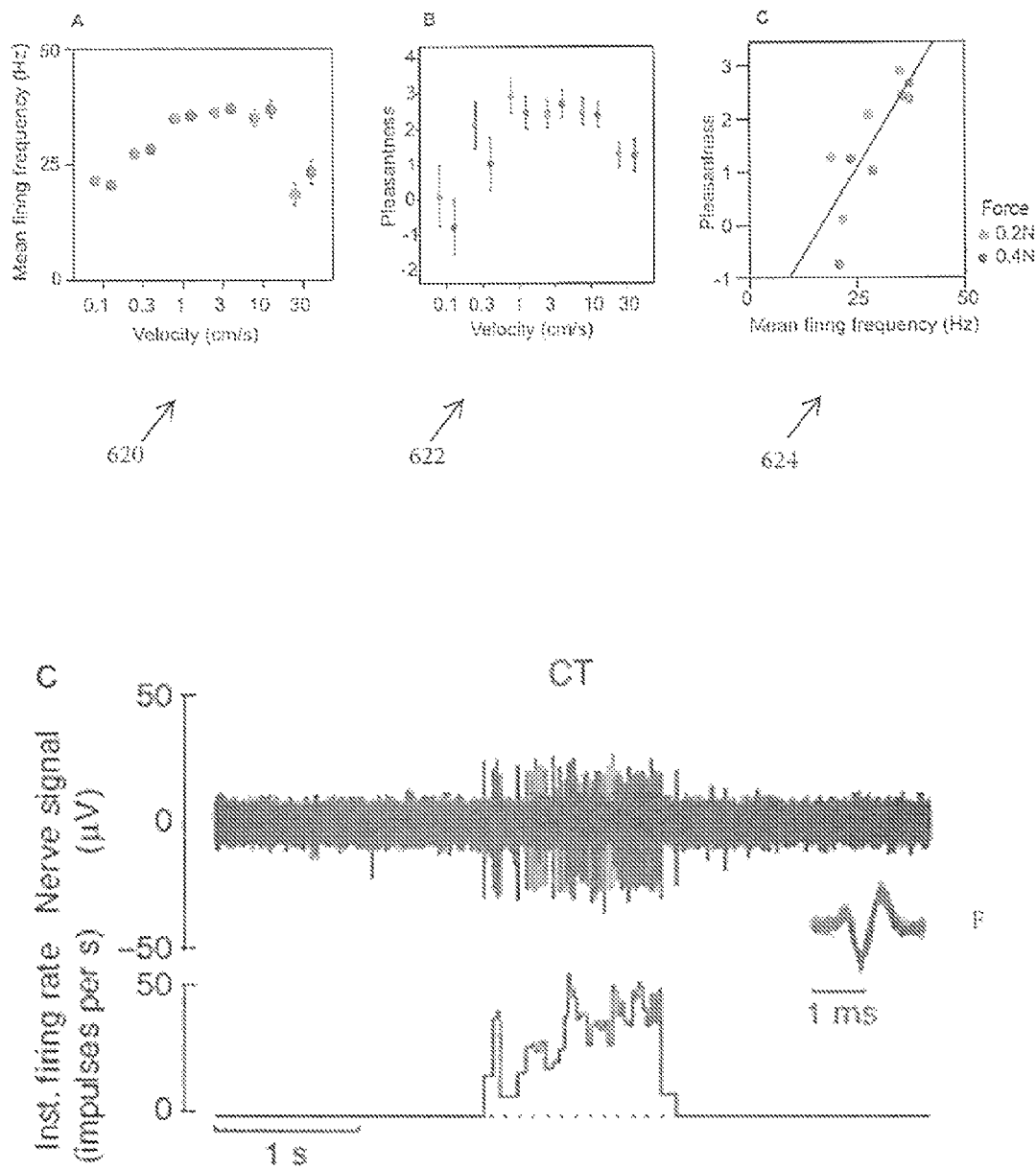
FIG. 6 illustrates a known relation between slow moving touch, a level of perceived pleasantness and firing frequency of C tactile fibers utilized in accordance with embodiments herein.

FIG. 6 illustrates a known relation between slow moving touch, a level of perceived pleasantness and firing frequency of C tactile fibers. In FIG. 6, graphs 620, 622 and 624 plot relations to various characteristics of interest. The graphs 620-624 are based on a 2009 paper by Loken L. S., Wessberg J., Morrison I., McGlone F., Olausson H. (2009), titled "Coding of pleasant touch by unmyelinated afferents in humans." Nat. Neurosci. 12, 547-548 10.1038/nn.2312. In the 2009 Loken paper, it was reported that pleasant touch sensations may begin with neural coding in the periphery by specific afferents. Loken found that during soft brush stroking, low-threshold unmyelinated mechanoreceptors (C-tactile), but not myelinated afferents, responded most vigorously at intermediate brushing velocities (1-10 cm s(-1)), which were perceived by subjects most pleasant.

The graph 622 plots the mean firing frequency (in impulses per second) associated with C tactile fibers along the vertical axis. The graph 622 plots, along the horizontal axis, the rate/velocity (in centimeters per second) at which the brushing, stroking or caressing sensation was applied across the forearm of the patient. The graph 622 plots data points associated with two different levels of force that were applied while introducing the brushing, stroking or caressing sensation across the patient's forearm. The two levels of force were a force of 0.2 N and a force of 0.4 N. As the rate at which the brushing sensation was increased from 0.1 to 10 cm/s, the mean firing frequency increased from 15 up to approximately 35 impulses per second. In addition, when a brushing sensation was introduced at a rate in the range of 1 to 10 cm/s, the mean firing frequency of C tactile fibers exhibited a local maximum level of between 35 and 40 impulses per second. However, when the rate at which the brushing sensation further increased to 30 cm/s, the mean firing frequency dropped to below 20 impulses per second, thereby indicating that C tactile fibers exhibit an upper rate limit to which the mean firing frequency will continue to increase. When the rate at which the sensation is applied exceeds the upper rate limit, the C tactile fibers exhibit a lower firing frequency.

Graph 624 illustrates a relation between the velocity (as indicated in centimeters per second along the horizontal axis) at which the brushing sensation was applied and a pleasantness or satisfaction rating assigned by the patient (as indicated along the vertical axis) a range of −2 to 4. The data points indicate that as the velocity of the brushing sensation was increased from 0.1 to 10 centimeters per second, the patient experienced increased pleasantness or satisfaction (ranging from −1 to 3). In addition, when the instrument was controlled to introduce a brushing sensation at a rate in the range of 1 to 10 cm/s, the patient experienced a local maximum level of pleasantness or satisfaction of between 2 and 3. However, as the velocity of the brushing sensation increased to 30 cm/s, the patient experienced a lower level of pleasantness or satisfaction (rated at 1). Hence, graph 624 indicates that the level of pleasantness or satisfaction experienced by the patient (that is at least partially introduced through excitation of C tactile fibers) increases as a velocity of the sensation varies over a select range. However, once the velocity of the sensation exceeds the upper limit of the select range, the patient begins to experience less pleasure or satisfaction from the sensation.

The graph 620 combines the information from the graphs 622 and 624 to plot the mean firing frequency of C tactile fibers along the horizontal axis and a pleasantness or satisfaction scale (as indicated by patients) along the vertical axis. The mean firing frequency corresponds to the rate at which the brushing sensation was applied across the patient's forearm. As the mean firing frequency (as measured in impulses per second) increases from approximately 10 to approximately 40 impulses per second, the measure of pleasantness or satisfaction denoted by the patient increased from a level of −1 to 3. Hence, graph 620 indicates that the level of pleasantness or satisfaction may be increased over a select mean firing frequency range (corresponding to the rate at which the sensation is moved along the patient's skin). In the example of FIG. 5, a select level of pleasantness or satisfaction may be introduced by exciting the C tactile fibers at a mean firing frequency of between 1 and 10 centimeters per second.

B. Firing Modes

Different firing modes or frequencies occur in the brain and/or other neuronal tissue, for example tonic firing and burst firing (irregular or regular burst firing). The thalamus utilizes both types of firing modes. The two thalami (bilateral paired structures) are the gateways to the cerebral cortex and, thus, to consciousness. The thalamic nuclei specialize in several different signaling functions: transmitting signals from sensory input to the cortex; transmitting signals from cortical motor centers to effectors; transmitting control signals that select which input and output will be permitted to pass to and from the cortex and how the signals will be sequenced (thalamic reticular nuclei (TRN)); and modulating (controlling intensity) and synchronizing (grouping) the signals (Intralaminar Nuclei (ILN)).

All thalamic relay neurons pass through the TRN, which opens and closes their "gates" going to the cortex, (McAlonan and Brown, 2002). One mode that TRN neurons use to transmit these relays is burst firing mode. This mode is useful for activating a small population of neurons in the cortex for a short period. In contrast, the continuous (tonic) firing mode permits a thalamic neuron to transmit a steady stream of signals to the cortex. The tonic firing pattern triggers looping activation in the cortical circuits that receive the signals. Evoking looping, or "recurrent" activation in the cortex requires a steady neural input.

The ILN are a tiny cluster of cells in the central body of the thalamus, hidden inside of the "laminae," the white layers that separate the bigger nuclei of the thalamus. In contrast to the bigger relay nuclei, most of the ILN send signals that change the activity of the cortical receiving area (Sherman and Guillery, 2002). For example, an ILN might receive signals from one cortical area and send them on to several other cortical areas to increase excitation in the receiving areas (a cortico-thalamo-cortical pattern, C-T-C).

Tonic or burst firing mode may be related to the molecules which are associated with the neurons. Such molecules include either parvalbumin (an egg-derived protein also a calcium-binding protein) or calbindin (a calcium-binding protein). Tonic firing is found especially in cells that contain parvalbumin. It behaves in a linear fashion, for example, the auditory thalamus (MGBV) fires at a specific frequency and the auditory cortex will follow at the same pace with a minor phase difference (Miller et al., 2001) of 2 ms. Tonic firing, however, can be overruled by burst firing (Lisman 1997; Sherman 2001; Swadlow and Gusev 2001).

Burst firing is typically found in calbindin positive cells (Kawaguchi and Kubota 1993; Hu et al., 1994; Hu 1995; He and Hu 2002). Thus, burst mode firing may utilize a calbindin system to generate the burst. Generally, burst firing is accomplished through the activation of either a subthreshold membrane conductance that initiates action potentials or a suprathreshold membrane conductance that once activated evokes two or more action potentials.

Burst firing acts in a non-linear fashion (Lisman 1997; Sherman 2001; Swadlow and Gusev 2001) with a summation effect of each spike, thus more readily activating a target cell (Lisman 1997) than tonic firing. Burst firing has been described in drowsiness, slow wave sleep, and anesthesia (Steriade et al., 1989; McCormick and Feeser 1990), as well as epilepsy (Futatsugi and Riviello 1998; Huguenard 1999) in the thalamus, and it functionally shuts off external auditory sensory stimuli to gain access to the cortex (Edeline et al., 2000; Massaux and Edeline 2003; Massaux et al., 2004), though not completely (Edeline et al., 2000). Neural network modeling has further demonstrated that bursts are generated by positive feedback through excitatory connections (Tabak and Latham 2003). In networks of two populations, one excitatory and one inhibitory, decreasing the inhibitory feedback can cause the network to switch from a tonically active, asynchronous state to the synchronized bursting state (van Vreeswijk and Hansel 2001).

The generation of repetitive burst discharges in neurons is correlated with the generation of gamma frequency (30-70 Hz) oscillations in the local field potential (Gray and Singer, 1989). It is believed that conscious perception depends on gamma band frequency activity (Gray and Singer, 1989; Joliot, 1994; Steriade, 2000).

III. Electrical Stimulation Devices

Figure 1B:
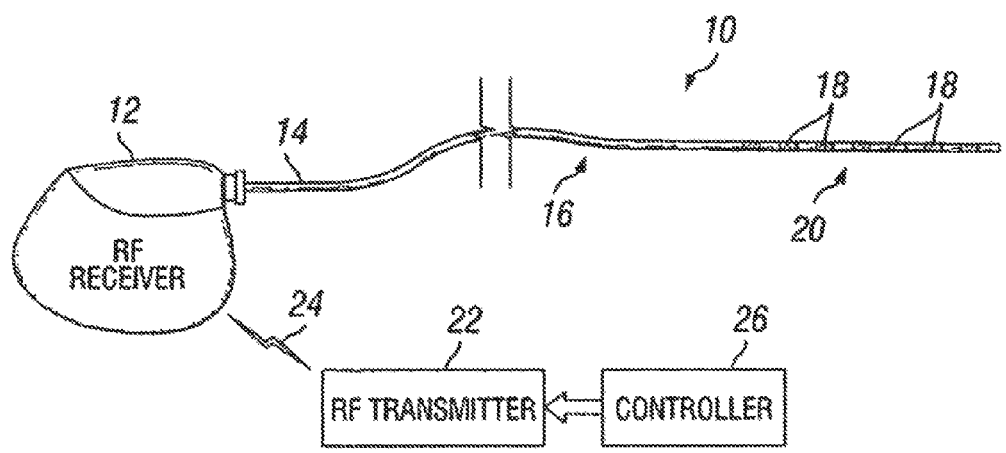
FIG. 1B illustrates an example neurological stimulation (NS) systems for electrically stimulating a predetermined site area to treat one or more neurological disorders or conditions in accordance with embodiments herein.

FIGS. 1A-1B illustrate example neurological stimulation (NS) systems 10 for electrically stimulating a predetermined site area to treat one or more neurological disorders or conditions. In general terms, stimulation system 10 includes an implantable pulse generating source or electrical IMD 12 (generally referred to as an "implantable medical device" or "IMD") and one or more implantable electrodes or electrical stimulation leads 14 for applying electrical stimulation pulses to a predetermined site. In operation, both of these primary components are implanted in the person's body, as discussed below. In certain embodiments, IMD 12 is coupled directly to a connecting portion 16 of stimulation lead 14. In other embodiments, IMD 12 is incorporated into the stimulation lead 14 and IMD 12 instead is embedded within stimulation lead 14. For example, such a stimulation system 10 may be a Bion® stimulation system manufactured by Advanced Bionics Corporation. Whether IMD 12 is coupled directly to or embedded within the stimulation lead 14, IMD 12 controls the stimulation pulses transmitted to one or more stimulation electrodes 18 located on a stimulating portion 20 of stimulation lead 14, positioned in communication with a predetermined site, according to suitable therapy parameters (e.g., duration, amplitude or intensity, frequency, pulse width, firing delay, etc.).

As contemplated in embodiments herein, a predetermined stimulation site for tissue of interest can include either peripheral neuronal tissue and/or central neuronal tissue. Neuronal tissue includes any tissue associated with the peripheral nervous system or the central nervous system. Peripheral neuronal tissue can include a nerve root or root ganglion or any neuronal tissue that lies outside the brain, brainstem or spinal cord. Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves.

Central neuronal tissue includes brain tissue, spinal tissue or brainstem tissue. Brain tissue can include thalamus/subthalamus, basal ganglia, hippocampus, amygdala, hypothalamus, mammilary bodies, substantia nigra or cortex or white matter tracts afferent to or efferent from the above-mentioned brain tissue, inclusive of the corpus callosum. Spinal tissue can include the ascending and descending tracts of the spinal cord, more specifically, the ascending tracts of that comprise intralaminar neurons or the dorsal column. The brainstem tissue can include the medulla oblongata, pons or mesencephalon, more particular the posterior pons or posterior mesencephalon, Lushka's foramen, and ventrolateral part of the medulla oblongata.

A doctor, the patient, or another user of IMD 12 may directly or in directly input therapy parameters to specify or modify the nature of the stimulation provided.

In FIG. 1B, the IMD 12 includes an implantable wireless receiver. An example of a wireless receiver may be one manufactured by Advanced Neuromodulation Systems, Inc., such as the Renew® System, part numbers 3408 and 3416. In another embodiment, the IMD can be optimized for high frequency operation as described in U.S. Provisional Application Ser. No. 60/685,036, filed May 26, 2005, entitled "SYSTEMS AND METHODS FOR USE IN PULSE GENERATION," which is incorporated herein by reference. The wireless receiver is capable of receiving wireless signals from a wireless transmitter 22 located external to the person's body. The wireless signals are represented in FIG. 1B by wireless link symbol 24. A doctor, the patient, or another user of IMD 12 may use a controller 26 located external to the person's body to provide control signals for operation of IMD 12. Controller 26 provides the control signals to wireless transmitter 22, wireless transmitter 22 transmits the control signals and power to the wireless receiver of IMD 12, and IMD 12 uses the control signals to vary the signal parameters of electrical signals transmitted through electrical stimulation lead 14 to the stimulation site. Thus, the external controller 26 can be for example, a handheld programmer, to provide a means for programming the IMD. An example wireless transmitter may be one manufactured by Advanced Neuromodulation Systems, Inc., such as the Renew® System, part numbers 3508 and 3516.

The IMD 12 applies burst stimulation to nerve tissue of a patient. Specifically, the IMD includes a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device.

The IMD 12 can be adapted by programming the microprocessor to deliver a number of spikes (relatively short pulse width pulses) that are separated by an appropriate interspike interval. Thereafter, the programming of the microprocessor causes the pulse generation module to cease pulse generation operations for an interburst interval. The programming of the microprocessor also causes a repetition of the spike generation and cessation of operations for a predetermined number of times. After the predetermined number of repetitions has been completed within a tactile stimulation waveform, the microprocessor can cause burst stimulation to cease for an amount of time (and resume thereafter). Also, in some embodiments, the microprocessor could be programmed to cause the pulse generation module to deliver a hyperpolarizing pulse before the first spike of each group of multiple spikes.

The microprocessor can be programmed to allow the various characteristics of the burst stimulus to be set by a physician to allow the burst stimulus to be optimized for a particular pathology of a patient. For example, the spike amplitude, the interspike interval, the interburst interval, the number of bursts to be repeated in succession, the electrode combinations, the firing delay between tactile stimulation waveforms delivered to different electrode combinations, the amplitude of the hyperpolarizing pulse, and other such characteristics could be controlled using respective parameters accessed by the microprocessor during burst stimulus operations. These parameters could be set to desired values by an external programming device via wireless communication with the implantable neuromodulation device.

In another embodiment, the IMD 12 can be implemented to apply burst stimulation using a digital signal processor and one or several digital-to-analog converters. The burst stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst parameters.

Figure 1C:
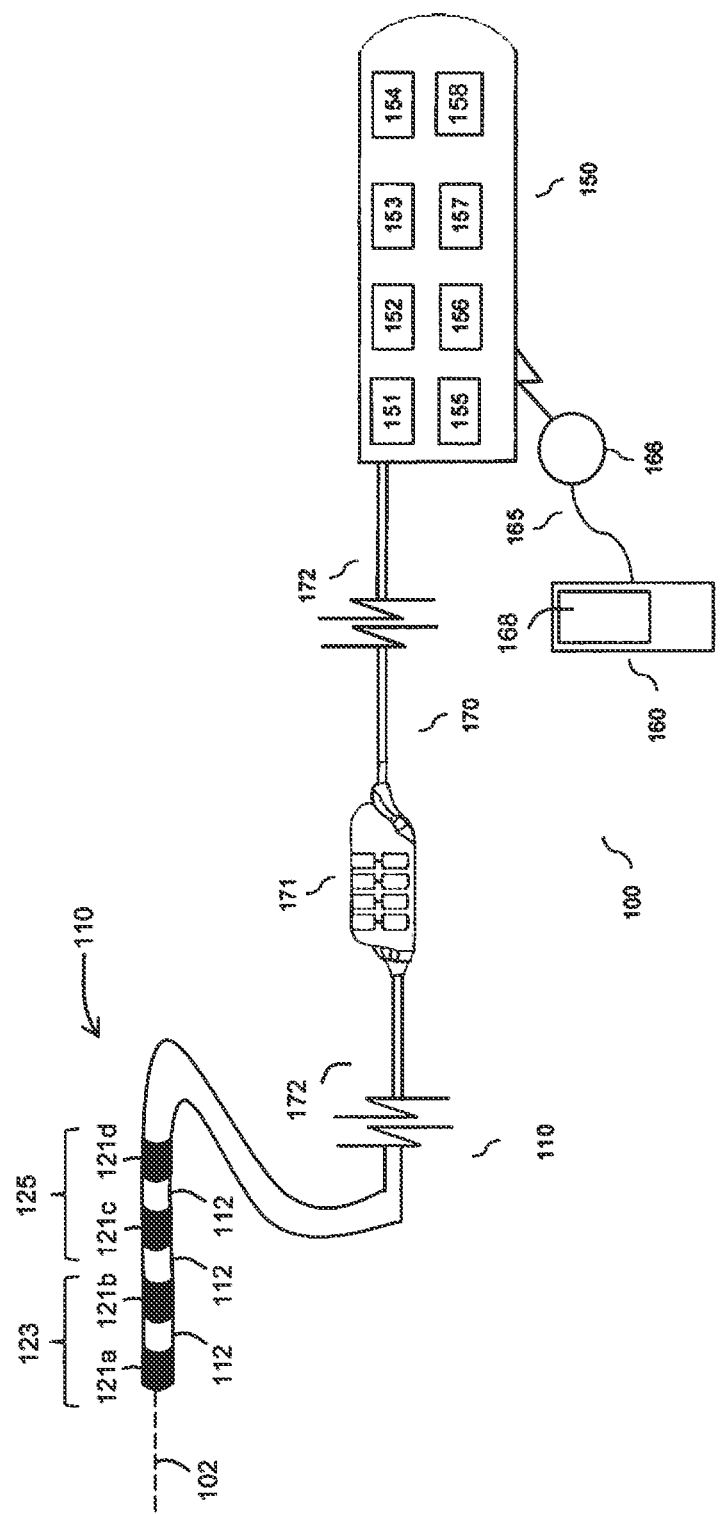
FIG. 1C depicts an NS system that delivers tactile therapies in accordance with embodiments herein.
Figure 2A:
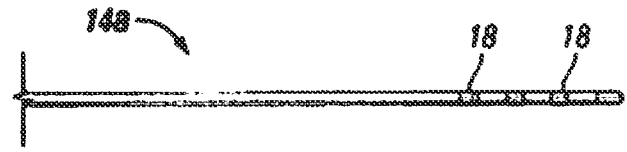
FIG. 2A illustrates example stimulation leads that may be used for electrically stimulating the predetermined site to treat one or more neurological disorders or conditions in accordance with embodiments herein.
Figure 2B:
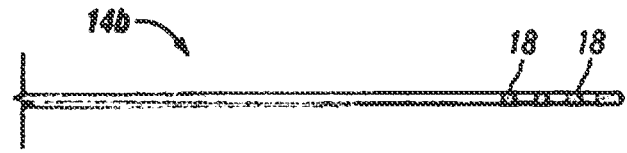
FIG. 2B illustrates example stimulation leads that may be used for electrically stimulating the predetermined site to treat one or more neurological disorders or conditions in accordance with embodiments herein.
Figure 2C:
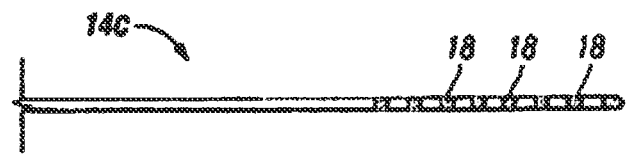
FIG. 2C illustrates example stimulation leads that may be used for electrically stimulating the predetermined site to treat one or more neurological disorders or conditions in accordance with embodiments herein.
Figure 2D:
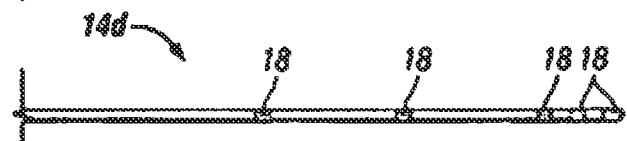
FIG. 2D illustrates example stimulation leads that may be used for electrically stimulating the predetermined site to treat one or more neurological disorders or conditions in accordance with embodiments herein.
Figure 2E:
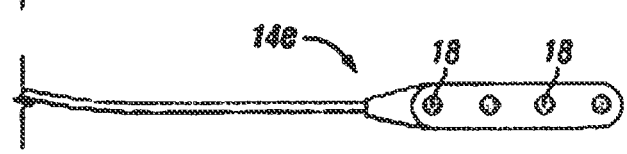
FIG. 2E illustrates example stimulation leads that may be used for electrically stimulating the predetermined site to treat one or more neurological disorders or conditions in accordance with embodiments herein.
Figure 2F:
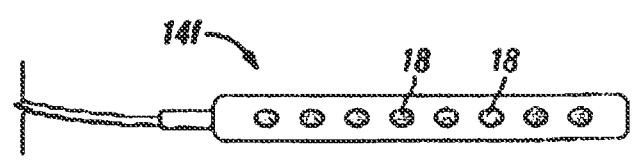
FIG. 2F illustrates example stimulation leads that may be used for electrically stimulating the predetermined site to treat one or more neurological disorders or conditions in accordance with embodiments herein.
Figure 2G:
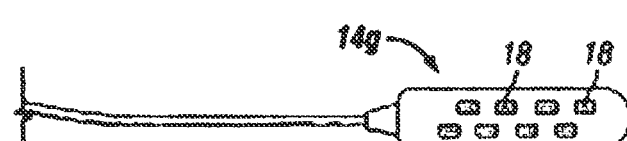
FIG. 2G illustrates example stimulation leads that may be used for electrically stimulating the predetermined site to treat one or more neurological disorders or conditions in accordance with embodiments herein.
Figure 2H:
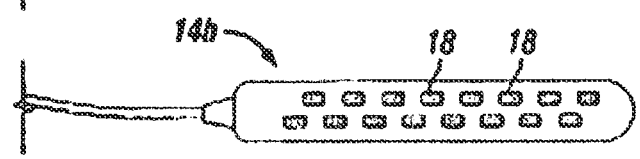
FIG. 2H illustrates example stimulation leads that may be used for electrically stimulating the predetermined site to treat one or more neurological disorders or conditions in accordance with embodiments herein.
Figure 2I:
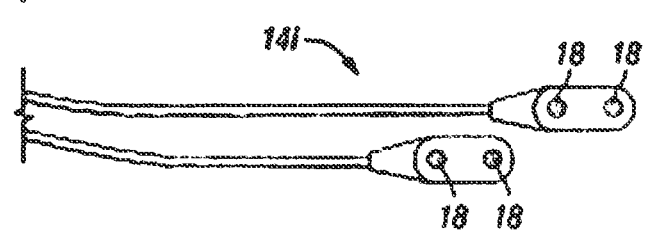
FIG. 2I illustrates example stimulation leads that may be used for electrically stimulating the predetermined site to treat one or more neurological disorders or conditions in accordance with embodiments herein.

FIG. 1C depicts an NS system 100 that delivers tactile therapies in accordance with embodiments herein. For example, the NS system 100 may be adapted to stimulate spinal cord tissue, peripheral nervous tissue, deep brain tissue, cortical tissue, cardiac tissue, digestive tissue, pelvic floor tissue, or any other suitable nervous tissue of interest within a patient's body.

The NS system 100 may be controlled to deliver various types of tactile stimulation therapy, such as high frequency neurostimulation therapies, burst neurostimulation therapies and the like. High frequency neurostimulation includes a continuous series of monophasic or biphasic pulses that are delivered at a predetermined frequency. Burst neurostimulation includes short sequences of monophasic or biphasic pulses, where each sequence is separated by a quiescent period. In general, tactile therapies include a continuous, repeating or intermittent pulse sequence delivered at a frequency and amplitude configured to avoid inducing (or introduce a very limited) paresthesia.

The NS system 100 may deliver tactile stimulation therapy based on preprogrammed therapy parameters. The therapy parameters may include, among other things, pulse amplitude, pulse polarity, pulse width, pulse frequency, interpulse interval, inter burst interval, electrode combinations, firing delay and the like. Optionally, the NS system 100 may represent a closed loop neurostimulation device that is configured to provide real-time sensing functions for C-fiber action potential (APs) from a lead. The configuration of the lead sensing electrodes that sense action potentials from the C fibers may be varied depending on the neuronal anatomy of the sensing site(s) of interest. The size and shape of electrodes is varied based on the implant location. The electronic components within the NS system 100 are designed with both stimulation and sensing capabilities, including alternative tactile stimulation therapy, such as burst mode, high frequency mode and the like.

The NS system 100 includes an implantable medical device (IMD) 150 that is adapted to generate electrical pulses for application to tissue of a patient. The IMD 150 typically comprises a metallic housing or can 158 that encloses a controller 151, pulse generating circuitry 152, a charge storage circuit 153, a battery 154, a far-field and/or near field communication circuitry 155, battery charging circuitry 156, switching circuitry 157, memory 158 and the like. The charge storage circuit 153 may represent one or more capacitors and/or battery cells that store charge used to produce the therapies described herein. The pulse generating circuitry 152, under control of the controller 151, manages discharge of the charge storage circuit 153 to shape the morphology of the waveform delivered while discharging energy. The switching circuitry 157 connects select combinations of the electrodes 121a-d to the pulse generating circuitry 152 thereby directing the stimulation waveform to a desired electrode combination. As explained herein, the switching circuitry 157 successively connects the pulse generating circuitry 152 to successive electrode combinations 123 and 125.

The controller 151 typically includes one or more processors, such as a microcontroller, for controlling the various other components of the device. Software code is typically stored in memory of the IMD 150 for execution by the microcontroller or processor to control the various components of the device.

The IMD 150 may comprise a separate or an attached extension component 170. If the extension component 170 is a separate component, the extension component 170 may connect with the "header" portion of the IMD 150 as is known in the art. If the extension component 170 is integrated with the IMD 150, internal electrical connections may be made through respective conductive components. Within the IMD 150, electrical pulses are generated by the pulse generating circuitry 152 and are provided to the switching circuitry 157. The switching circuitry 157 connects to outputs of the IMD 150. Electrical connectors (e.g., "Bal-Seal" connectors) within the connector portion 171 of the extension component 170 or within the IMD header may be employed to conduct various stimulation pulses. The terminals of one or more leads 110 are inserted within connector portion 171 or within the IMD header for electrical connection with respective connectors. Thereby, the pulses originating from the IMD 150 are provided to the lead 110. The pulses are then conducted through the conductors of the lead 110 and applied to tissue of a patient via stimulation electrodes 121a-d that are coupled to blocking capacitors. Any suitable known or later developed design may be employed for connector portion 171.

The stimulation electrodes 121a-d may be positioned along a horizontal axis 102 of the lead 110, and are angularly positioned about the horizontal axis 102 so the stimulation electrodes 121a-d do not overlap. The stimulation electrodes 121a-d may be in the shape of a ring such that each stimulation electrode 121a-d continuously covers the circumference of the exterior surface of the lead 110. Adjacent stimulation electrodes 121a-d are separated from one another by non-conducting rings 112, which electrically isolate each stimulation electrode 121a-d from an adjacent stimulation electrode 121a-d. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121a-d may be configured to emit the pulses in an outward radial direction proximate to or within a stimulation target. Additionally or alternatively, the stimulation electrodes 121a-d may be in the shape of a split or non-continuous ring such that the pulse may be directed in an outward radial direction adjacent to the stimulation electrodes 121a-d. The stimulation electrodes 121a-d deliver tonic, high frequency and/or burst tactile stimulation waveforms as described herein. Optionally, the electrodes 121a-d may also sense sensory action potential (SAP signals) for a data collection window. Optionally, the electrodes 121a-d may include a microelectrode located immediately adjacent C-fibers. Optionally, the IMD 150 may sense a C tactile sensory action potential (SAP) directly at the microelectrode and perform an iterative feedback loop to adjust at least one therapy parameter based on the C tactile SAP.

The lead 110 may comprise a lead body 172 of insulative material about a plurality of conductors within the material that extend from a proximal end of lead 110, proximate to the IMD 150, to its distal end. The conductors electrically couple a plurality of the stimulation electrodes 121 to a plurality of terminals (not shown) of the lead 110. The terminals are adapted to receive electrical pulses and the stimulation electrodes 121a-d are adapted to apply the pulses to the stimulation target of the patient. Also, sensing of physiological signals may occur through the stimulation electrodes 121a-d, the conductors, and the terminals. It should be noted that although the lead 110 is depicted with four stimulation electrodes 121a-d, the lead 110 may include any suitable number of stimulation electrodes 121a-d (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for any embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile.

By way of example, the IMD 12, 150 may include a processor and associated charge control circuitry as described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IMD using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference. An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IMD 12, 150. Different burst and/or high frequency pulses on different stimulation electrodes may be generated using a single set of the pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads as is also known in the art. Various sets of parameters may define the pulse characteristics and pulse timing for the pulses applied to the various stimulation electrodes. Although constant current pulse generating circuitry is contemplated for some embodiments, any other suitable type of pulse generating circuitry may be employed such as constant voltage pulse generating circuitry.

The controller 151 delivers a tactile stimulation waveform to at least one electrode combination located proximate to nervous tissue of interest, the tactile stimulation waveform including a series of pulses configured to excite the tactile C-fibers of the nervous tissue of interest, the tactile stimulation waveform defined by therapy parameters. The controller 151 may deliver the tactile stimulation waveform based on preprogrammed therapy parameters. The preprogrammed therapy parameters may be set based on information collected from numerous past patients and/or test performed upon an individual patient during initial implant and/or during periodic checkups.

Optionally, the controller 151 senses sensory action potential (SAP) signals from at least one electrode on the lead. Optionally, the controller 151 analyzes the SAP signals to obtain activity data for a SAP C-fiber component (tactile or nociceptive). The controller 151 determines whether the activity data satisfies a criteria of interest. The controller 151 adjusts at least one of the therapy parameters to change the tactile stimulation waveform when the activity data does not satisfy the criteria of interest.

The controller 151 iteratively repeats the delivering operations for a group of TPS. The IMD analyzes the tactile SAP signals to obtain activity data associated with the TPS for the tactile SAP C-fiber components, the analyzing operations obtaining a collection of activity data associated with the group of TPS. The IMD selects a candidate TPS from the group of TPS based on a criteria of interest. The therapy parameters define at least one of a burst stimulation waveform or a high frequency stimulation waveform. The controller 151 may repeat the delivering, sensing and adjusting operations to optimize the tactile stimulation waveform. The analyzing operation may include analyzing a feature of interest from a morphology of the SAP signal over time, counting a number of occurrences of the feature of interest that occur within the SAP signal over a predetermined duration, and generating the activity data based on the number of occurrences of the feature of interest.

Memory 158 stores software to control operation of the controller 151 for tactile stimulation therapy as explained herein. The memory 158 also stores SAP signals, therapy parameters, SAP activity level data, sensation scales and the like. For example, the memory 158 may save SAP activity level data for various different therapies as applied over a short or extended period of time. A collection of SAP activity level data is accumulated for different therapies and may be compared to identify high, low and acceptable amounts of sensory activity for the tactile C-fibers that result from different therapies.

A controller device 160 may be implemented to charge/recharge the battery 154 of the IMD 150 (although a separate recharging device could alternatively be employed) and to program the IMD 150 on the pulse specifications while implanted within the patient. Although, in alternative embodiments separate programmer devices may be employed for charging and/or programming the NS system 100. The controller device 160 may be a processor-based system that possesses wireless communication capabilities. Software may be stored within a non-transitory memory of the controller device 160, which may be executed by the processor to control the various operations of the controller device 160. A "wand" 165 may be electrically connected to the controller device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IMD 150. Optionally, in some embodiments, the wand 165 may comprise one or more temperature sensors for use during charging operations.

The user may initiate communication with the IMD 150 by placing the wand 165 proximate to the NS system 100. Preferably, the placement of the wand 165 allows the telemetry system of the wand 165 to be aligned with the far-field and/or near field communication circuitry 155 of the IMD 150. The controller device 160 preferably provides one or more user interfaces 168 (e.g., touchscreen, keyboard, mouse, buttons, or the like) allowing the user to operate the IMD 150. The controller device 160 may be controlled by the user (e.g., doctor, clinician) through the user interface 168 allowing the user to interact with the IMD 150. The user interface 168 may permit the user to move electrical stimulation along and/or across one or more of the lead(s) 110 using different stimulation electrode 121 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the controller device 160 may permit operation of the IMD 12, 150 according to one or more therapies to treat the patient. Each therapy may include one or more sets of stimulation parameters of the pulse including pulse amplitude, pulse width, pulse frequency or inter-pulse period, firing delay, pulse repetition parameter (e.g., number of times for a given pulse to be repeated for respective stimset during execution of program), biphasic pulses, monophasic pulses, etc. The IMD 150 modifies its internal parameters in response to the control signals from the controller device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

FIGS. 2A-2I illustrate example stimulation leads 14 that may be used for electrically stimulating the predetermined site to treat one or more neurological disorders or conditions. As described above, each of the one or more stimulation leads 14 incorporated in stimulation systems 10, 100 includes one or more stimulation electrodes 18 adapted to be positioned in communication with the predetermined site and used to deliver the stimulation pulses received from IMD 12 (or pulse generating circuitry 157 in FIG. 1C). A percutaneous stimulation lead 14 (corresponding to the lead 110 in FIG. 1C), such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (e.g., generally perpendicular to the axis of stimulation lead 14) in all directions. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, embodiments herein contemplate stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site in one side of the head, while bilateral electrical stimulation of the predetermined site may be accomplished using two stimulation leads 14 implanted in communication with the predetermined site in opposite sides of the head.

In one embodiment, the stimulation source is transcutaneously in communication with the electrical stimulation lead. In "transcutaneous" electrical nerve stimulation (TENS), the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

The IMD 12, 150 allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting nerve tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

In embodiments herein, the therapy parameter of signal frequency is varied to achieve a burst type rhythm, or burst mode stimulation. Generally, the burst stimulus frequency may be in the range of about 1 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. As another example, the burst stimulus frequency may be in the range of 10-80 Hz. Each burst stimulus comprises at least two spikes, for example, each burst stimulus can comprise about 2 to about 100 spikes, more particularly, about 2 to about 10 spikes. Each spike can comprise a frequency in the range of about 50 Hz to about 1000 Hz, more particularly, in the range of about 200 Hz to about 500 Hz. The frequency for each spike within a burst can be variable, thus it is not necessary for each spike to contain similar frequencies, e.g., the frequencies can vary in each spike. The inter-spike interval can be also vary, for example, the inter-spike interval, can be about 0.5 milliseconds to about 100 milliseconds or any range therebetween.

Optionally, the burst stimulus may include noise stimulation as a stimulation design. For example, the burst stimulus morphology for the spikes may represent a noise pattern/shape during each burst interval. Optionally, a noise signal may be modulated onto pulses within the bursts.

The burst stimulus is followed by an inter-burst interval, during which substantially no stimulus is applied. The inter-burst interval has duration in the range of about 5 milliseconds to about 5 seconds, more preferably, 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz), 145 msec to about 80 msec (8-12 Hz) or 1 to 5 seconds in plateau potential firing. The burst stimulus and the inter-burst interval can have a regular pattern or an irregular pattern (e.g., random or irregular harmonics). More specifically, the burst stimulus can have a physiological pattern or a pathological pattern.

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

FIGS. 2A-2I respectively depict stimulation portions for inclusion at the distal end of lead. Stimulation portion depicts a conventional stimulation portion of a "percutaneous" lead with multiple ring electrodes. Stimulation portion depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion includes multiple planar electrodes on a paddle structure.

Figure 3:
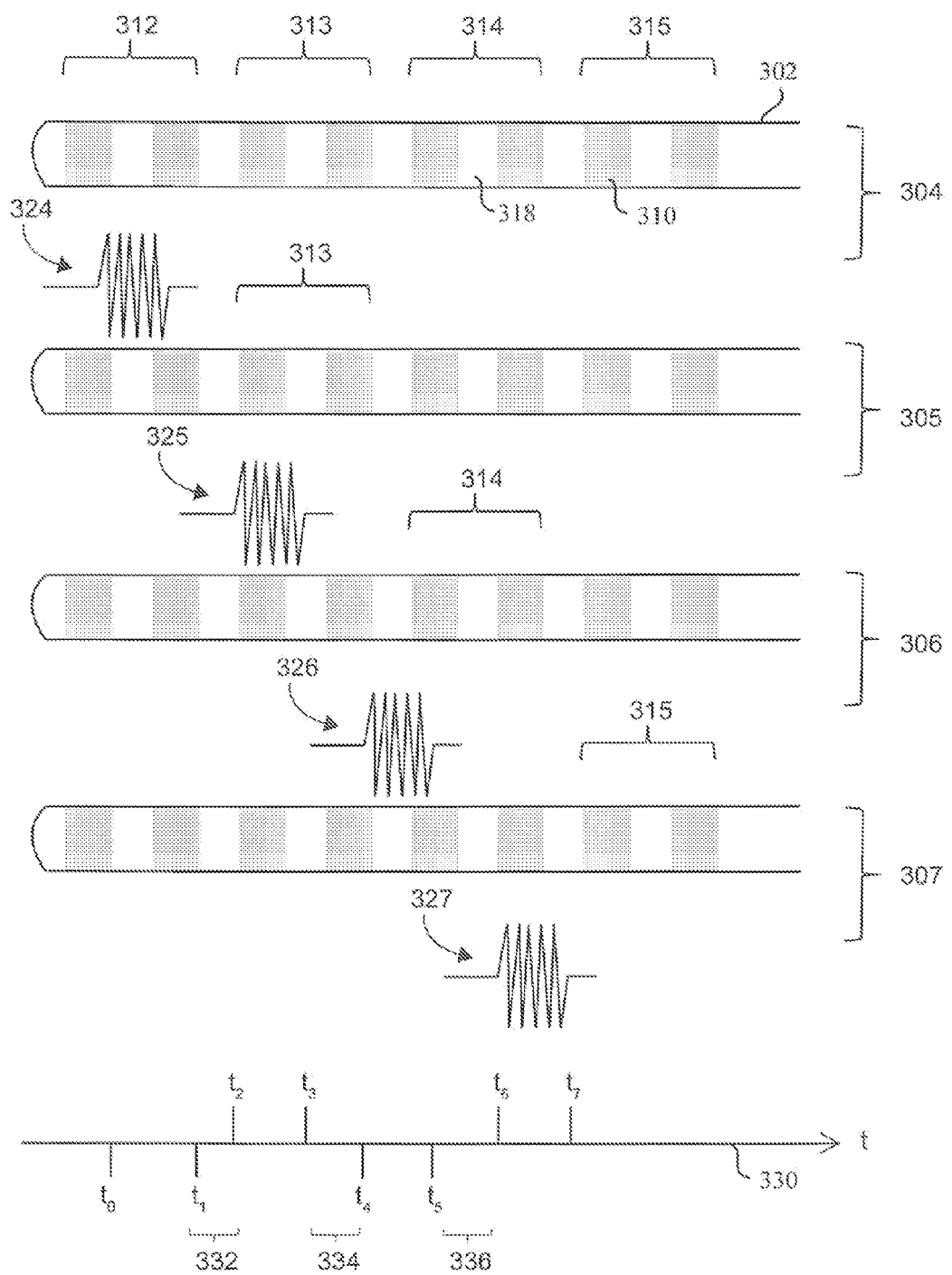
FIG. 3 illustrates a distal portion of a lead in connection with a timing diagram for delivering tactile stimulation waveforms in accordance with embodiments herein.

FIG. 3 illustrates a distal portion of a lead in connection with a timing diagram for delivering tactile stimulation waveforms in accordance with embodiments herein. The distal portion 302 is located proximate to nervous tissue of interest (e.g., spinal tissue, brain tissue, etc.). The distal portion 302 of a single lead is illustrated multiple times in connection with a series of successive activation events 304-307. The distal portion 302 includes an array of electrodes 310 that are arranged in electrode combinations 312-315. The electrode combinations 312-315 are arranged along a length of the lead body 318 and positioned adjacent to one another. As explained herein, one or more processors within the IMD 12, 150 manages delivery of the tactile stimulation waveforms to the electrode combinations 312-315 in a temporal, serial manner such that adjacent electrode combinations 312-315 deliver corresponding tactile stimulation waveforms at non-overlapping distinct points in time.

A horizontal axis 330 is illustrated to denote time and includes a series of timing markers T0-T7. The activation events 304-307 are temporally separated from one another in a non-overlapping manner along the horizontal axis 330. For example, the activation events 304-307 occurs between discrete times T0-T1, times T2-T3, times T4-T5 and times T6-T7, respectively. During the activation events 304-307, a common or different tactile stimulation waveforms 324-327 are delivered to corresponding electrode combinations 312-315.

During the activation event 304, a first tactile stimulation waveform 324 is delivered to a first electrode combination 312 within the array of electrodes 310 between times T0 and T1. Following termination of tactile stimulation waveform 324 at time T1, the IMD 12, 150 waits for the duration of a firing delay 332 until time T2. At time T2, a second tactile stimulation waveform 325 is delivered through a second electrode combination 313. Following termination of the tactile stimulation waveform 325 at time T3, the IMD 12, 150 waits for the duration of a firing delay 334 until time T4. At time T4, a third tactile stimulation waveform 326 is delivered through a third electrodes combination 314. Following termination of the tactile stimulation waveform 326 at time T5, the IMD 12, 150 waits for another firing delay 336 until time T6 at which time, tactile stimulation waveform 327 is delivered through electrode combination 315. The foregoing process may be repeated for any desired number of electrode combinations along the lead.

Figure 4:
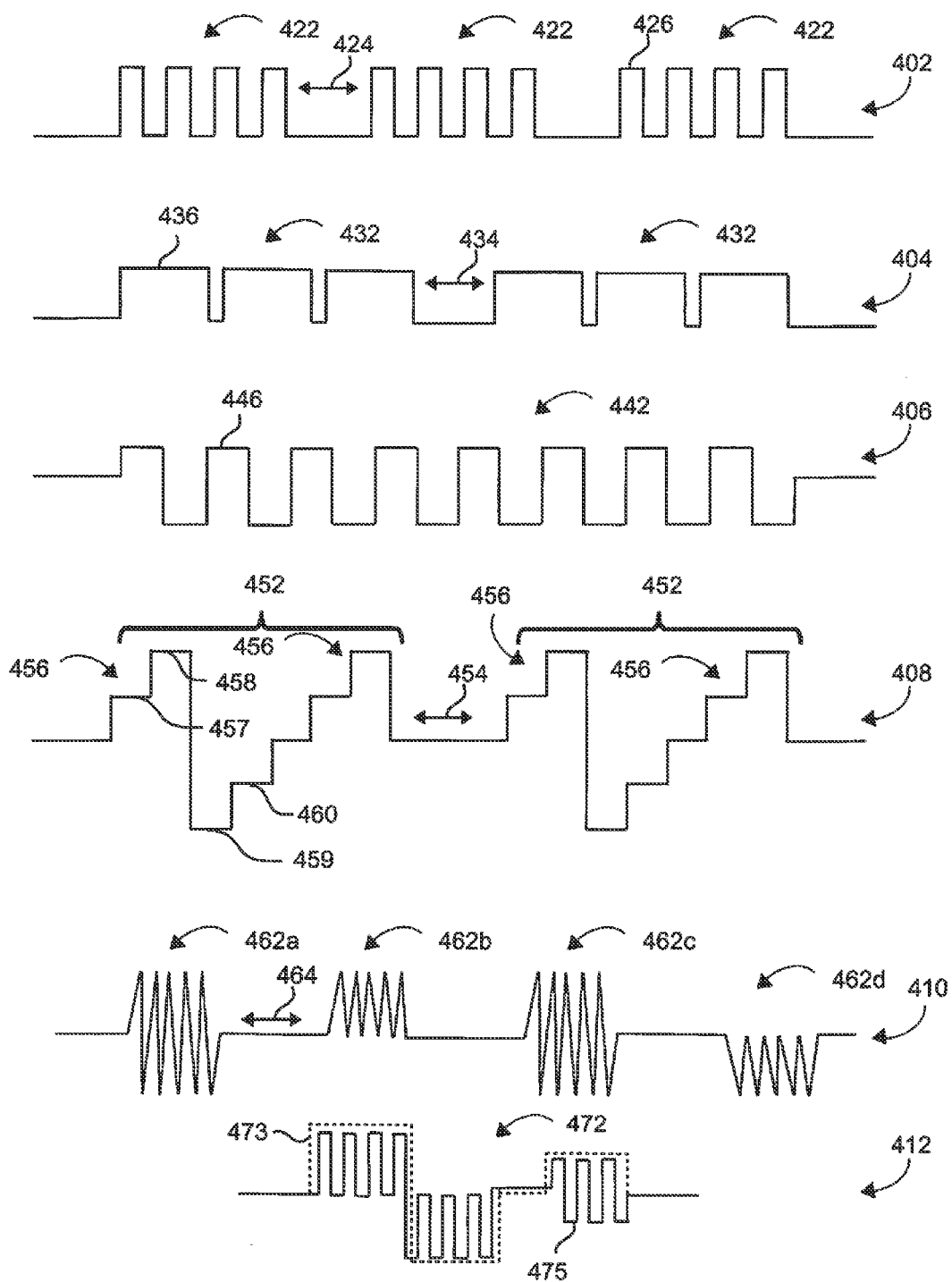
FIG. 4 illustrates alternative tactile stimulation waveforms that may be utilized in accordance with embodiments herein.

In the example of FIG. 3, the tactile stimulation waveforms 324-327 each are illustrated as a single pulse burst including a predetermined number of pulses/spikes that alternate between positive and negative polarities and have a common pulse amplitude. Optionally, the waveforms 324-327 may include multiple pulse bursts, one or more tonic pulses, as well as other waveforms. FIG. 4 illustrates examples of other waveforms. During any one or more of the waveforms 324, as one example, the pulses/spikes may alternate polarity at a desired pulse frequency, such as 40 Hz and the like. The IMD 12, 150 steps between different electrode combinations 312-315 along the distal portion 302 in a temporal serial manner such that the adjacent electrode combinations 312-315 deliver corresponding tactile stimulation waveforms 324-327 at non-overlapping distinct points in time. The IMD 12, 150 sequentially steps through adjacent electrode combinations (e.g. 312 and 313, 313 and 314, 314 and 315) such that the waveforms 324-327 are progressively delivered at a distinct activation sites along the distal portion 302 of the lead. The IMD 12, 150 also sequentially steps through the adjacent electrode combinations at an activation rate defined by the firing delays 332-336. The firing delays 332-336 are set, such that the activation rate corresponds to a select pleasant tactile input. For example, it may be determined that a pleasant feeling is introduced by caressing, gently stroking or grooming a select portion of a patient (e.g., an arm, leg, back, face). As noted above, a pleasant feeling is introduced by rubbing a patient's arm at a rate/velocity between 1 and 10 cm/s. Accordingly, the electrode combinations 312-315 are excited as distinct activations sites at an activation rate that results in the desired/target feeling.

In the present example, the activation rate is set to generally correspond to the rate at which a desired anti-nociceptive tactile input is applied. For example, to achieve an activation rate of 1-10 cm/s, the firing delay between successive electrode combinations is adjusted based on various characteristics such as the shape and dimensions of the lead. The firing delay may be set based on the length of the distal portion of the lead and the spacing between adjacent electrode combinations. For example, adjacent electrode combinations may be spaced 5 mm apart (e.g., as measured from the centers of the nearest electrodes, from the centers of the electrode combinations, from the centers of adjacent activation sites). It may be desirable to set the firing delay to 0.1 seconds for adjacent electrode combinations, such that every 0.1 sec. a stimulation waveform (324-327) is delivered from successive electrode combinations (e.g., 312-315 in FIG. 3). In the foregoing example, the stimulation waveform would advance in a step-wise manner in 0.5 cm (5 mm) increments along the lead every 0.1 s thereby achieving an activation rate of 5 cm/s (50 mm in 1 second).

As a further example, adjacent electrode combinations may be spaced 1 cm apart. It may be desirable to set the firing delay to 0.1 seconds for adjacent electrode combinations, such that every 0.25 sec. a stimulation waveform is delivered from successive electrode combinations (e.g., 312-315 in FIG. 3). In the foregoing example, the stimulation waveform would advance in a step-wise manner from electrode combination 312 to combination 313, to combination 314, etc., every 0.25 s thereby achieving an activation rate of 4 cm/s.

Optionally, the activation rate may vary from the rate associated with the anti-nociceptive tactile input (e.g., rate at which the patient's arm is rubbed). For example, it may be determined that a patient experiences increased pleasure when C tactile fiber stimulation is applied to electrode combinations at a rate that is slightly higher or slightly lower than the rate at which tactile inputs are applied to the patient's skin.

The tactile stimulation waveforms 324-327 utilize pulse amplitudes, pulse widths and pulse frequencies that are below the lower excitation threshold associated with the nociceptive C fibers and excitation of A-delta and A-beta fibers. As noted above, nociceptive C fibers are excited by stimulation waveforms corresponding to a noxious input applied at or greater than 2.5 mN. Accordingly, the pulse amplitude, pulse width and pulse frequency for the tactile stimulation waveforms 324-327 are set to remain below an input at 2.5 mN.

In the example of FIG. 3, each electrode combination 312-315 includes two electrodes 310. Optionally, more than two electrodes may be included in one or more of the electrode combinations 312-315. For example, each electrode combination 312-315 may include three, four or more electrodes. Optionally, the electrode combinations 312-315 may include different numbers of electrodes. For example, electrode combination 312 may include 4 electrodes, while electrode combination 314 may include two electrodes. Also, the array of electrodes 310 is illustrated as a one-dimensional array extending along the length of a lead body 318 that is generally tubular in shape and elongated to extend along a central longitudinal axis. Optionally, the lead body 318 may be formed in other manners, as illustrated in FIGS. 2A-2I. The array of electrodes 310 may be varied, such as to resemble the electrode arrays illustrated in FIGS. 2A-2I. As a further example, the array of electrodes 310 may be provided on a paddle shaped lead body having multiple rows and multiple columns (e.g. a 3×10 array, a 5×5 array, a 5×10 array, a 10×10 array, a 5×20 array, etc.).

FIG. 4 illustrates alternative tactile stimulation waveforms that may be utilized in accordance with embodiments herein. In FIG. 4, the tactile stimulation waveforms 402-412 are delivered during activation events utilizing a corresponding electrode combination. The tactile stimulation waveforms 402-412 may be delivered from multiple electrode combinations along the lead, such as corresponding to the activation events 304-307 in FIG. 3. The tactile stimulation waveform 402 includes multiple (e.g. three) pulse bursts 422 separated by an inter-burst interval 424, with the pulse bursts 422 delivered from a common electrode combination before therapy moves to a different electrode combinations. The pulse burst 422 include a series of pulses 426 having a common polarity (e.g. all positive pulses or all negative pulses).

The tactile stimulation waveform 404 includes a pair of pulse bursts 432 separated by an interburst interval 434. Each pulse burst 432 includes a series of pulses 436 (e.g. three) that have a common polarity. The tactile stimulation waveform 406 includes a single pulse burst 442 having a series of pulses 446, each of which is bipolar (e.g. extends between positive and negative polarities). The pulses 446 have one of two states/voltage levels, namely a positive pulse amplitude and a negative pulse amplitude that are common.

The stimulation waveform 408 includes a pair of pulse bursts 452 separated by an inter-burst interval 454. Each pulse burst 452 includes multiple pulses 456 that are bipolar (extending between positive and negative polarities). The pulses 456 vary between more than two states or voltage levels, namely first and second positive voltages 457-458 and first and second negative voltages 459 and 460. Optionally, additional voltage levels/states may be utilized and the positive and negative voltage levels need not be common.

The tactile stimulation waveform 410 includes pulse burst 462A-462D, that are separated by an interburst interval 464. The interburst intervals 464 may differ from one another or be common. The pulse bursts 462A and 462C have similar positive and negative amplitudes, while the pulse bursts 462B (positive) and 462D (negative) are monopolar and different from one another. The tactile stimulation waveform 412 illustrates a single pulse burst 472 that has a carrier wave (as denoted by envelope 473 in dashed lines) that is modulated by a higher frequency signal (as denoted by solid lines 475). Optionally, the tactile stimulation waveform may be varied from the foregoing examples. Additionally, separate and distinct tactile stimulation waveforms may be delivered from different electrode combinations at non-overlapping distinct points in time. With reference to the electrode and activation states of FIG. 3, a first electrode combination 312 may deliver the tactile stimulation waveform 402 with a first polarity (such as illustrated in FIG. 4), while the second electrode combination 313 delivers the same tactile stimulation waveform 402, but with an opposite polarity. As a further example, the first electrode combination 312 may deliver one of the tactile stimulation waveforms 402-412, while the second electrode combination 313 delivers another of the tactile stimulation waveforms 402-412.

Figure 5A:
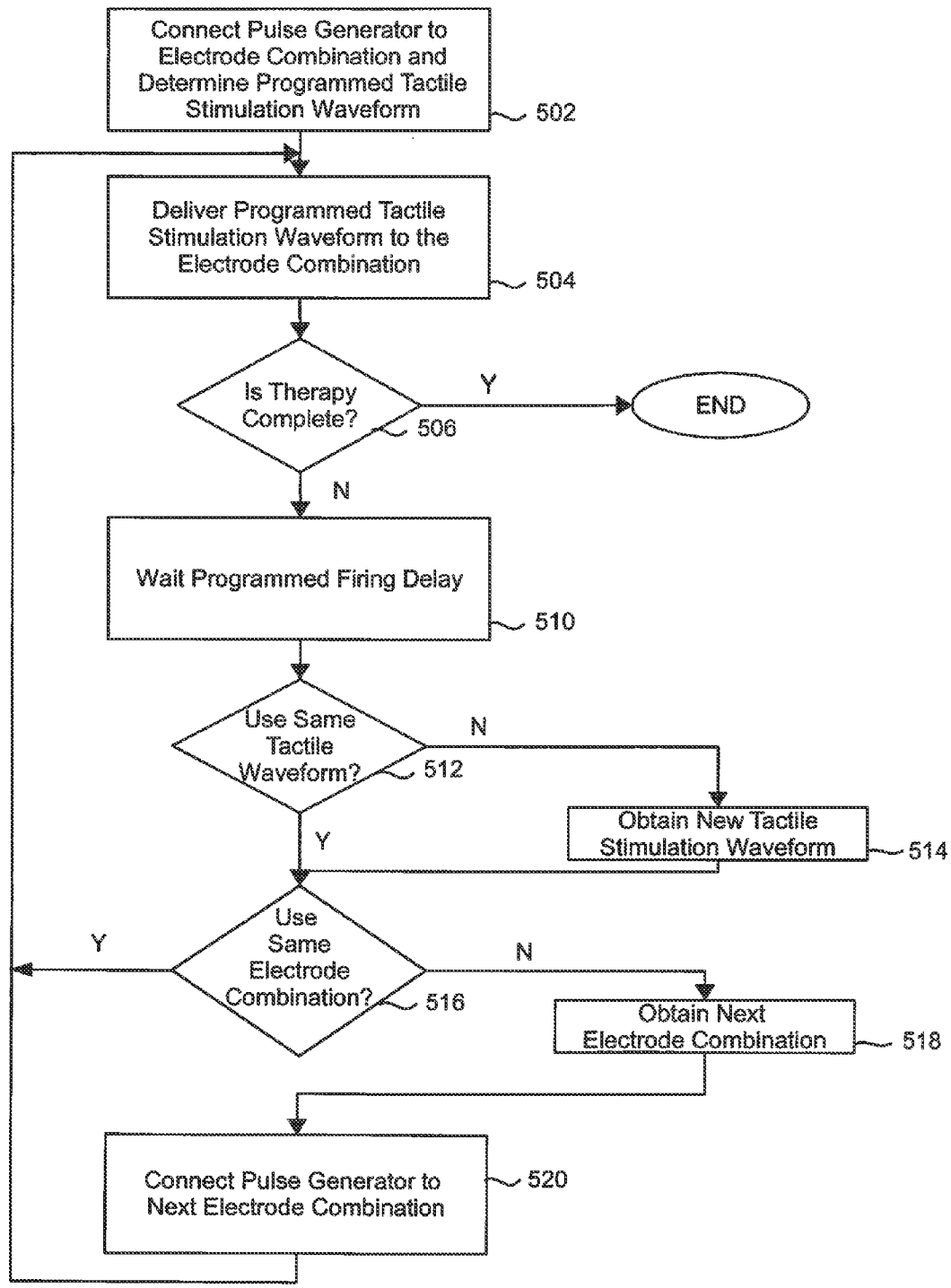
FIG. 5A illustrates a process for controlling C tactile fiber stimulation of nervous tissue of a patient in accordance with embodiments herein.

FIG. 5A illustrates a process for controlling C tactile fiber stimulation (e.g. burst and/or high frequency) of nervous tissue of a patient in accordance with embodiments herein. The operations of FIG. 5 may be implemented by one or more processors, such as within an implantable medical device, external programmer, another external device and the like. The IMD, external programmer or other external device are coupled to a lead having at least one stimulation electrode that is implanted at a target position proximate to nervous tissue of interest.

FIG. 5A illustrates a process for managing the delivery of C tactile fiber stimulation to nervous tissue of a patient in accordance with embodiments herein. At 502, the IMD manages a switch circuit to connect the pulse generator to a select electrode combination as defined by a programmed therapy parameter set. At 502, the IMD also determines the tactile stimulation waveform to be utilized. The stimulation waveform is defined by one or more parameters forming a therapy parameter set (TPS). Examples of therapy parameters within a TPS include, but are not limited to pulse amplitude, pulse width, interpulse delay, number of pulses per burst, pulse frequency, burst frequency, etc. The TPS is defined such that the stimulation waveform is configured to excite C tactile fibers and not excite nociceptive C-fibers at the target position. The stimulation waveform is also configured to not excite A-Delta or A-Beta fibers at the target position.

At 504, the IMD delivers a tactile stimulation waveform to the current electrode combination within the array of electrodes located proximate to nervous tissue of interest. The stimulation waveform is delivered to at least one stimulation electrode combination on the lead. The stimulation waveform may represent a pulse burst formed from a series of monophasic pulses (with a positive or negative current pulse) or a series of biphasic waveform (with positive and negative pulses). When the stimulation waveform is biphasic, a first pulse phase may be configured to capture at least a portion of the C tactile fibers, while the second pulse phase is configured to repolarize charge at a stimulation site. By repolarizing charge at the stimulation site, the second pulse phase limits an extent of C-fiber excitation (e.g., a degree to which, or amount of, the fibers of interest are excited).

At 506, the IMD determines whether the therapy is complete. When the therapy is complete, the process ends. Otherwise, the process continues to 510. At 510, the IMD waits the programmed firing delay.

At 512, the IMD determines whether to use the same tactile stimulation waveform or to use a different tactile stimulation waveform. When the same waveform is to be utilized, flow moves two 516. Otherwise, flow advances to 514. At 514, the IMD obtains the next or successive tactile stimulation waveform to be utilized. Thereafter, flow moves to 516.

At 516, the IMD determines whether to use the same electrode combination as with the prior activation event. If so, flow returns to 504. Otherwise, flow advances to 518. At 518, the IMD obtains the next electrode combination to be utilized. At 520, the IMD manages the switch to connect the pulse generator to the corresponding next electrode combination. Thereafter, flow returns to 504.

The operations of FIG. 5A are continuously repeated indefinitely, periodically or for a select period of time. In accordance with the foregoing manner, the IMD sequentially delivering (through the operations at 504-520) successive tactile stimulation waveforms to successive electrode combinations within the array of electrodes, the first and successive tactile stimulation waveforms including at least one series of pulses having a pulse amplitude and pulse frequency. The IMD delays delivery of the successive tactile stimulation waveforms by the firing delay at 510. The IMD manages at least one of the therapy parameters of the first and successive tactile stimulation waveforms to excite C tactile fibers of the nervous tissue of interest, without exciting A Beta, A Delta or, C nociceptive fibers.

The foregoing process of FIG. 5A presumes that the IMD operates in accordance with the preprogrammed therapy parameter set that is defined by a physician, clinician, the patient or otherwise. The therapy parameter set may be determined in various manners, such as based upon data collected from numerous studies, prior patients, the present patient over time and the like.

Figure 5B:
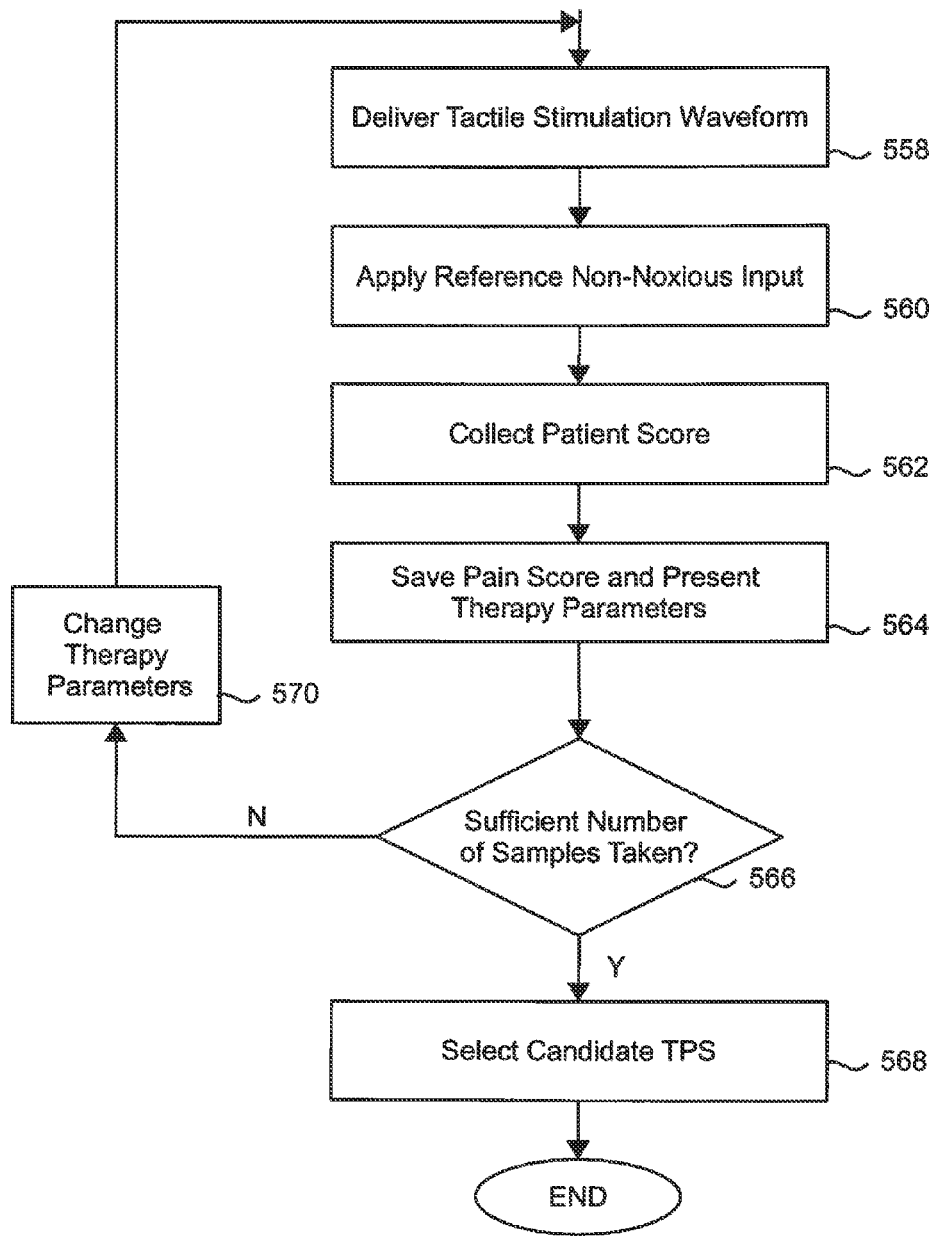
FIG. 5B illustrates a process for determining a therapy parameter set to be utilized in connection with an individual patient in accordance with embodiments herein.

FIG. 5B illustrates a process for determining a therapy parameter set to be utilized in connection with an individual patient in accordance with embodiments herein. During implant or during subsequent checkups, the process of FIG. 5B may be carried out in order to collect and analyze activity data in connection with multiple therapy parameter sets, while collecting feedback information from the patient. The feedback information may be collected while the patient is present with the physician or clinician. Alternatively, the feedback may be collected over a longer period of time, such as when the nature of the feedback requires additional time for the patient to determine the effectiveness of a particular therapy parameter set (e.g. when assessing depression, or other mental states that are not immediately apparent) for example, the patient may leave the doctor's office while one parameter set is programmed. The patient may return after some period of time to provide feedback regarding the current therapy parameter set, at which time a new therapy parameter set is programmed and the patient may again leave the doctor's office.

The IMD defines one or more tactile stimulation waveforms and electrode combinations to be used. At 558, the IMD delivers the tactile stimulation waveform. At 560, optionally, the IMD applies a predetermined external sensory stimulation as a reference input that is configured to excite the fibers of interest (e.g. tactile C-fibers). The reference input may represent a predetermined degree or amount of touch, pressure, brushing motion, or any other nonnoxious external input intended to otherwise cause activity within the fibers of interest. The reference input is applied in a repeatable manner such that a common amount of touch, pressure and the like may be applied repeatedly at different times while SAP signals are collected in connection with different TPS. At 562, the patient enters a sensation score to indicate an amount/degree of pleasure experienced by the patient relative to a predetermined sensation index. Optionally, 560 may be omitted entirely and the sensation score used as the sole/primary feedback.

At 564, the IMD saves the sensation score, along with the values for the corresponding therapy parameter set, such as in a memory of the IMD, external programmer or other external device. The sensation scores and the associated therapy parameter set are saved, over time, in connection with delivering therapy based on multiple therapy parameter sets, thereby developing a therapy/sensitivity history for the patient and/or for a collection of patients. The therapy/sensitivity history indicates, among other things, a degree to which certain therapies inhibit sensory action potentials along conduction nerve fibers of interest (e.g., the C-fibers).

In the embodiment illustrated in FIG. 5B, the operation at 564 may be implemented during each iteration through the operation at 558-570. Optionally, the operation at 564 may be implemented once after an entire collection of activity data is obtained from a predetermined number of iterations through the operations at 558-570 for the group or multiple different combinations of therapy parameter sets.

At 566, the IMD determines whether a sufficient number of samples have been collected (and analyzed). When a sufficient number of samples have been collected, flow moves to 568. When it is determined that additional samples should be collected, flow moves to 570. The determination at 566 may be based on a satisfaction level experienced by the patient. For example, at 566, it may be determined whether the patient sensation score is sufficiently high in connection with the current therapy parameter set. Alternatively, the decision at 566 may be determined based on a desire to collect at least a minimum number of data samples. For example, it may be determined that 10 or more separate therapy parameter sets should be analyzed to obtain a sufficient amount of data in connection with the patient before programming a particular tactile stimulation waveform.

At 570, the IMD changes a value for one or more of the parameters within the therapy parameter set. The change at 570 may be performed in a predetermined systematic stepwise manner. For example, each parameter within the therapy parameter set may be incrementally adjusted by a select amount during separate iterations through the operations. As an example, during iterations 1-5, the IMD may only change the amplitude of the stimulation waveform between low, medium and high amplitudes, while maintaining constant all other parameters within the TPS. After cycling through each of the pulse amplitudes of interest, the pulse amplitude may be reset to the low level for iterations 5-6, during which the pulse width is changed from short to medium to long. During iterations 7-9, the pulse amplitude may be set to the medium level, while the pulse width is again changed from short to medium to long, while the firing delay between successive pulse burst delivered by successive electrode combinations is adjusted while other parameters are maintained constant. The foregoing process may be repeated until each, or at least a select portion, of the potential permutations and combinations of levels for the parameters are used during the operations at 558-570 to form the group of TPS for which the collection of activity data is accumulated.

Alternatively or additionally, not all permutations and combinations of parameter levels may be used. For example, a physician or other user may select (and/or program) individual TPS of interest to be tested as the group of TPS. For example, the operations at 558-570 may only be repeated for 5 to 10 or 20 different TPS, even though many more permutations and combinations of levels for the various parameters exist. The change performed at 570 may be based on pre-stored settings or may represent an input from a physician or other user during operation.

Optionally, the amount of change during each iteration through 570 may vary, such as with larger step changes made during initial iterations and smaller step changes made during later iterations. Optionally, the amount of change at 570 may be based on a difference between the activity data and the threshold. For example, when the activity data substantially exceeds the threshold, larger changes may be applied to one or more parameters at 570. As the difference between the activity data and threshold decreases, the incremental change in the one or more parameters is changed by similarly/proportionally decreasing amounts. Following 570, flow returns to 558.

The operations at 558-570 build a database, file, or generally a sensation-activity data relation corresponding to a relation between therapy parameter sets and sensation scores indicative of a level of pain experienced by the patient.

At 568, the IMD (and/or the physician and patient) selects a candidate TPS from the multiple or group of TPS based on one or more criteria of interest. For example, when the criteria of interest represents a threshold or predetermined range for the activity data, the candidate TPS may be selected as the TPS that resulted in the lowest sensation score and/or the highest level of tactile pleasure. Once a candidate TPS is selected, the candidate TPS is used for subsequent therapy for a period of time, for example until it becomes desirable to repeat the process of FIG. 5B to determine a new candidate TPS.

The operations of FIG. 5B may be repeated for a number of different therapy parameter sets. For example, it may be desirable to obtain activity data in connection with 5, 10 or more than 10 different stimulation waveforms, in order to derive a more complete understanding of a particular patient's neural fiber activity respond to different stimulation waveforms. When a sufficient amount of activity data is collected, the process ends and the candidate TPS is selected and implemented.

IV. Implantation Of Electrical Devices

The stimulation systems 10, 100, described above, can be implanted into a person's body with stimulation lead 14, 110 located in communication with a predetermined site. It is envisioned that the predetermined site can be a central or peripheral neuronal tissue.

A. Deep Brain Stimulation

In certain embodiments, for example, patients may have an electrical stimulation lead or electrode implanted into the brain. The anatomical targets or predetermined site may be stimulated directly or affected through stimulation in another region of the brain.

In embodiments herein, the predetermined site or implant sites include, but are not limited to thalamus/sub-thalamus, basal ganglia, hippocampus, amygdala, hypothalamus, mammillary bodies, substantia nigra or cortex or white matter tracts afferent to or efferent from the abovementioned brain tissue, inclusive of the corpus callosum. Still further, the predetermined site may comprise the auditory cortex and/or somatosensory cortex in which the stimulation devices is implanted cortically.

Once electrical stimulation lead 14, 110 has been positioned in the brain, lead 14, 110 is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14, 110 is laid substantially flat along the skull. Where appropriate, any burr hole cover seated in the burr hole may be used to secure electrical stimulation lead 14, 110 in position and possibly to help prevent leakage from the burr hole and entry of contaminants into the burr hole.

Once electrical stimulation lead 14, 110 has been inserted and secured, connecting portion of lead 14, 110 extends from the lead insertion site to the implant site at which IMD 12, 150 is implanted. The implant site is typically a subcutaneous pocket formed to receive and house IMD 12, 150. The implant site is usually positioned a distance away from the insertion site, such as near the chest, below the clavicle or alternatively near the buttocks or another place in the torso area. Once all appropriate components of stimulation system 10, 100 are implanted, these components may be subject to mechanical forces and movement in response to movement of the person's body. A doctor, the patient, or another user of IMD 12, 150 may directly or in directly input signal parameters for controlling the nature of the electrical stimulation provided.

Although example steps are illustrated and described, embodiments herein contemplate two or more steps taking place substantially simultaneously or in a different order. In addition, embodiments herein contemplate using methods with additional steps, fewer steps, or different steps, so long as the steps remain appropriate for implanting an example stimulation system 10, 100 into a person for electrical stimulation of the person's brain.

B. Spinal and Peripheral Neuronal Tissue

Electrical energy can be delivered through electrodes positioned external to the dura layer surrounding the spinal cord. Stimulation on the surface of the cord (subdurally) is also contemplated, for example, stimulation may be applied to the dorsal columns as well as to the dorsal root entry zone or the dorsal root ganglia and/or nerve root. In accordance with embodiments herein, the lead may be located in various areas along the spinal cord, such as at the cervical vertebral segment C2. C2 may represent potential tissue of interest as a somatotopic representation of the entire body exists at the rostrocaudal length of C2-C3 and the caudal extent of the NTS exists at C2. The spinothalamic and nonspinothalamic cells at C2 have receptive fields covering the entire body. Also, the C2 cells do not play a substantial role in sensory discriminative function. Instead, the C2 cells behave as reticular formation cells and have an arousal function for the thalamus. In accordance with embodiments herein, methods and devices apply tactile stimulation therapy to tissue proximate to C2, thereby affording a strong anti-nociceptive effect on the entire body as C tactile fibers are anti-nociceptive.

Optionally, other areas of the spinal cord (besides C2) may be stimulated in embodiments herein for example the any neuronal tissue associated with any of the cervical vertebral segments (C1, C3, C4, C5, C6, C7 and C8) and/or any tissue associated with any of the thoracic vertebral segments (T1, T2, T3, T4, T5, T6, T7, T8, T9, T10, T11, 12) and/or any tissue associated with any of the lumbar vertebral segments (L1, L2, L3, L4. L5, L6) and/or any tissue associated with the sacral vertebral segments (S1, S2, S3, S4, S5). Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves. In addition peripheral nerves also includes the nerves of the autonomic nervous system, including both sympathetic and parasympathetic system Stimulation electrodes 18 may be positioned in various body tissues and in contact with various tissue layers; for example, subdural, subarachnoid, epidural, cutaneous, transcutaneous and subcutaneous implantation is employed in some embodiments. The electrodes are carried by two primary vehicles: a percutaneous leads and a laminotomy lead.

In certain embodiments, one or more stimulation electrodes 18 are positioned in communication with a peripheral nerve. Stimulation electrodes 18 are commonly positioned in communication with the peripheral nerve by electrodes applied cutaneously to the dermatome area of a peripheral nerve. Stimulation electrodes 18 can be positioned subcutaneously in communication with the peripheral nerve or on the nerve root ganglion.

For spinal cord stimulation, percutaneous leads commonly have two or more, equally-spaced electrodes, which are placed above the dura layer through the use of a Touhy-like needle. For insertion, the Touhy-like needle is passed through the skin, between desired vertebrae, to open above the dura layer. For unilateral stimulation, percutaneous leads are positioned on a side of a spinal column corresponding to the "afflicted" side of the body, as discussed above, and for bilateral stimulation, a single percutaneous lead is positioned along the patient midline (or two or more leads are positioned on each side of the midline).

C. Brainstem Stimulation

The stimulation system 10, 100, described above, can be implanted into a person's body with stimulation lead 14 located in communication with a predetermined brainstem tissue and/or area. Such systems that can be used are described in WO2004062470, which is incorporated herein by reference in its entirety.

The predetermined brainstem tissue can be selected from medulla oblongata, pons or mesencephalon, more particular the posterior pons or posterior mesencephalon, Lushka's foramen, and ventrolateral part of the medulla oblongata.

Implantation of a stimulation lead 14 in communication with the predetermined brainstem area can be accomplished via a variety of surgical techniques that are well known to those of skill in the art. For example, an electrical stimulation lead can be implanted on, in, or near the brainstem by accessing the brain tissue through a percutaneous route, an open craniotomy, or a burr hole. Where a burr hole is the means of accessing the brainstem, for example, stereotactic equipment suitable to aid in placement of an electrical stimulation lead 14 on, in, or near the brainstem may be positioned around the head. Another alternative technique can include, a modified midline or retrosigmoid posterior fossa technique.

In certain embodiments, electrical stimulation lead 14 is located at least partially within or below the aura mater adjacent the brainstem. Alternatively, a stimulation lead 14 can be placed in communication with the predetermined brainstem area by threading the stimulation lead up the spinal cord column, as described above, which is incorporated herein.

As described above, each of the one or more leads 14 incorporated in stimulation system 10 includes one or more electrodes 18 adapted to be positioned near the target brain tissue and used to deliver electrical stimulation energy to the target brain tissue in response to electrical signals received from IMD 12. A percutaneous lead 14 may include one or more circumferential electrodes 18 spaced apart from one another along the length of lead 14. Circumferential electrodes 18 emit electrical stimulation energy generally radially in all directions and may be inserted percutaneously or through a needle. The electrodes 18 of a percutaneous lead 14 may be arranged in configurations other than circumferentially, for example as in a "coated" lead 14. A laminotomy or paddle style lead 14, such as example leads 14*e-i*, includes one or more directional electrodes 18 spaced apart from one another along one surface of lead 14. Directional electrodes 18 emit electrical stimulation energy in a direction generally perpendicular to the surface of lead 14 on which they are located. Although various types of leads 14 are shown as examples, embodiments herein contemplate stimulation system 10 including any suitable type of lead 14 in any suitable number, including three-dimensional leads and matrix leads as described below. In addition, the leads may be used alone or in combination.

Yet further, a stimulation lead 14 can be implanted in communication with the predetermined brainstem area by a using stereotactic procedures similar to those described above, which are incorporated herein, for implantation via the cerebrum.

Still further, a predetermined brainstem area can be in directly stimulated by implanting a stimulation lead 14 in communication with a cranial nerve (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve in directly stimulates the predetermined brainstem tissue. Such techniques are further described in U.S. Pat. Nos. 6,721,603; 6,622,047; and 5,335,657, and U.S. Provisional Application 60/591,195 entitled "Stimulation System and Method for Treating a Neurological Disorder" each of which are incorporated herein by reference.

Although example steps are illustrated and described, embodiments herein contemplate two or more steps taking place substantially simultaneously or in a different order. In addition, embodiments herein contemplate using methods with additional steps, fewer steps, or different steps, so long as the steps remain appropriate for implanting stimulation system 10 into a person for electrical stimulation of the predetermined site.

In accordance with embodiments herein, methods and devices afford activation of the anti-nociceptive system of the human body. For example, the methods and systems may utilize tactile stimulation therapies to treat chronic neuropathic pain, various syndromes, fibromyalgia, and in general nociceptive pain. By activating pleasure responses of the human body, methods and devices are provided to treat depression, social isolation or deprivation, distress, anxiety, autism and the like. Further, by activating pleasure responses of the human body, methods and devices are provided to treat homeostatic imbalances, such as irritable bowel syndrome (IBS), urinary urgency, pain, tinnitus, addiction, obesity and the like.

Embodiments are described herein for applying tactile C-fiber stimulation to address various indications. The tactile C-fiber stimulation activates the antinociceptive system to counteract chronic neuropathic pain syndromes, fibromyalgia, nociceptive pain and the like. The tactile C-fiber stimulation seeks to activate pleasure sensations which may also counteract depression, social isolation or deprivation, distress, anxiety, autism and the like. In addition, the tactile C-fiber stimulation may be used to offset homestatic imbalances such as irritable bowel syndrome, urinary urgency, pain, tinnitus, addiction, obesity and the like.

In accordance with embodiments herein, the methods and systems described herein may be applied to deliver tactile C-fiber stimulation in place or in combination with the therapies described in U.S. Pat. No. 8,897,870, entitled "Stimulation Design for Neuromodulation", issuing on Nov. 25, 2014, the complete subject matter of which is expressly incorporated herein by reference in its entirety including any and all patents and publications referenced and incorporated by reference into the '870 patent. In accordance with further embodiments, the methods and systems described herein may be applied to deliver tactile C-fiber stimulation in place or in combination with the therapies described in U.S. Pat. No. 8,682,441, entitled "Use of a New Stimulation Design to Treat Neurological Disorder", issuing on Mar. 25, 2014, the complete subject matter of which is expressly incorporated herein by reference in its entirety including any and all patents and publications referenced and incorporated by reference into the '441 patent.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. When processor-based, the controller executes program instructions stored in memory to perform the corresponding operations. Additionally or alternatively, the controllers and the controller device may represent circuits that may be implemented as hardware. The above examples are exemplary only, and are thus not intended to limit in any way the definition and/or meaning of the term "controller."

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 45 U.S.C. §112(f), unless and until such claim limitations expressly use the phrase "means for" followed by a statement of function void of further structure.

What is claimed is:

1. A method to deliver C tactile fiber stimulation to nervous tissue of a patient, the method comprising;
    delivering a first tactile stimulation waveform to a first electrode combination within a plurality of electrodes located proximate to nervous tissue of interest;
    sequentially delivering successive tactile stimulation waveforms to successive electrode combinations within the plurality of electrodes, the first and successive tactile stimulation waveforms including at least one series of pulses having a pulse amplitude and pulse frequency, wherein the series of pulses includes a group of spikes that begin and end at the pulse amplitude, the pulse amplitude being set to avoid excitation of nociceptive C fibers;
    delaying delivery of the successive tactile stimulation waveforms by a firing delay, the pulse amplitude, pulse frequency and firing delay representing therapy parameters;
    managing at least one of the therapy parameters of the first and successive tactile stimulation waveforms to excite C tactile fibers of the nervous tissue of interest.

2. The method of claim 1, wherein the firing delay includes a substantially quiescent period between the first and successive tactile stimulation waveforms.

3. The method of claim 1, wherein the firing delay between successive pairs of the multiple tactile stimulation waveforms is between one and 10 cm/s.

4. The method of claim 3, wherein the delivering operations are repeated for multiple tactile stimulation waveforms in connection with corresponding electrode combinations in the array, wherein excitation of successive pairs of the multiple tactile stimulation waveforms is separated by the firing delay to correspond to a velocity at which C tactile fibers convey signals.

5. The method of claim 1, wherein the series of pulses are organized into pulse bursts.

6. The method of claim 1, wherein the plurality of electrodes are disposed in a linear array of electrodes arranged along a length of an electrode body.

7. The method of claim 1, wherein the pulse frequency is approximately 40 Hz.

8. A system to control C tactile fiber stimulation of nervous tissue of a patient, the system comprising:
    a lead having a plurality of stimulation electrodes, the lead configured to be implanted at a target position proximate to nervous tissue of interest; and
    an implantable medical device (IMD) coupled to the lead, the IMD including a processor and memory storing programmable instructions, the processor executing the programmable instructions to:
        sequentially deliver tactile stimulation waveforms to a series of electrode combinations within the plurality of stimulation electrodes, the tactile stimulation waveforms including at least one series of pulses having a pulse amplitude and pulse frequency;
        delay delivery of the successive tactile stimulation waveforms relative to one another by a firing delay, the pulse amplitude, pulse frequency and firing delay representing therapy parameters, wherein the firing delay corresponds to an activation rate of between 1 and 10 cm/s; and
        manage at least one of the therapy parameters such that the successive tactile stimulation waveforms excites C tactile fibers of the nervous tissue of interest.

9. The system of claim 8, wherein the electrode combinations in the series are arranged along a body of the lead and positioned adjacent to one another, the processor delivering the tactile stimulation waveforms to the electrode combinations in a temporal serial manner such that adjacent electrode combinations deliver corresponding tactile stimulation waveforms at nonoverlapping distinct points in time.

10. The system of claim 8, wherein the processor sequentially steps through adjacent electrode combinations such that the tactile stimulation waveforms are progressively delivered at distinct activation sites along the lead at an activation rate corresponding to a corresponding non-noxious tactile input.

11. The system of claim 8, wherein the IMD includes a pulse generator and a switch circuit that couples the pulse generator to a corresponding one of the electrode combinations when delivering a corresponding tactile stimulation waveform.

12. The system of claim 8, wherein the IMD includes a switch circuit that defines individual channels between the IMD and each of the electrode combinations, the tactile stimulation waveforms being delivered over corresponding channels at non-overlapping points in time.

* * * * *